US00RE50301E

(19) United States
(12) Reissued Patent
Marom et al.

(10) Patent Number: US RE50,301 E
(45) Date of Reissued Patent: *Feb. 18, 2025

(54) DEPOT SYSTEMS COMPRISING GLATIRAMER OR PHARMACOLOGICALLY ACCEPTABLE SALT THEREOF

(71) Applicant: MAPI PHARMA LTD., Ness Ziona (IL)

(72) Inventors: Ehud Marom, Tel Aviv (IL); Shai Rubnov, Tel Aviv (IL)

(73) Assignee: Mapi Pharma Ltd., Ness Ziona (IL)

( * ) Notice: This patent is subject to a terminal disclaimer.

(21) Appl. No.: 17/894,447

(22) Filed: Aug. 24, 2022

Related U.S. Patent Documents

Reissue of:
(64) Patent No.: 8,377,885
Issued: Feb. 19, 2013
Appl. No.: 13/408,472
Filed: Feb. 29, 2012

U.S. Applications:
(63) Continuation of application No. 17/213,352, filed on Mar. 26, 2021, now Pat. No. Re. 49,251, which is an application for the reissue of Pat. No. 8,377,885, which is a continuation-in-part of application No. 13/258,808, filed as application No. PCT/IL2010/000679 on Aug. 19, 2010, now Pat. No. 8,796,226.

(60) Provisional application No. 61/291,928, filed on Jan. 4, 2010.

(51) Int. Cl.

| | |
|---|---|
| ***C07K 14/00*** | (2006.01) |
| ***A61K 9/00*** | (2006.01) |
| ***A61K 9/16*** | (2006.01) |
| ***A61K 9/19*** | (2006.01) |
| ***A61K 9/50*** | (2006.01) |
| ***A61K 38/02*** | (2006.01) |

(52) U.S. Cl.
CPC ..... *C07K 14/001* (2013.01); *A61K 9/0024* (2013.01); *A61K 9/1647* (2013.01); *A61K 9/19* (2013.01); *A61K 9/5031* (2013.01); *A61K 38/02* (2013.01); *Y10T 428/2982* (2015.01)

(58) Field of Classification Search
CPC .. C07K 14/001; A61K 9/0024; A61K 9/1647; A61K 9/19; A61K 9/5031; A61K 38/02; Y10T 428/2982; A61P 25/00; A61P 37/04
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,773,919 | A | 11/1973 | Boswell |
| 3,845,770 | A | 11/1974 | Theeuwes |
| 3,849,550 | A | 11/1974 | Teitelbaum |
| 3,916,899 | A | 11/1975 | Theeuwes |
| 4,008,719 | A | 2/1977 | Theeuwes |
| 4,822,340 | A | 4/1989 | Kamstra |
| 5,059,595 | A | 10/1991 | Le Grazie |
| 5,073,543 | A | 12/1991 | Marshall |
| 5,120,548 | A | 6/1992 | McClelland |
| 5,354,556 | A | 10/1994 | Sparks |
| 5,578,442 | A | 11/1996 | Desai |
| 5,591,767 | A | 1/1997 | Mohr |
| 5,639,476 | A | 6/1997 | Oshlack |
| 5,643,605 | A | 7/1997 | Cleland |
| 5,674,533 | A | 10/1997 | Santus |
| 5,733,559 | A | 3/1998 | Citernesi |
| 5,800,808 | A | 9/1998 | Konfino |
| 5,858,964 | A | 1/1999 | Aharoni |
| 5,945,126 | A | 8/1999 | Thanoo et al. |
| 5,981,589 | A | 11/1999 | Konfino |
| 6,048,898 | A | 4/2000 | Konfino |
| 6,054,430 | A | 4/2000 | Konfino |
| 6,214,791 | B1 | 4/2001 | Arnon |
| 6,309,669 | B1 | 10/2001 | Setterstrom |
| 6,342,476 | B1 | 1/2002 | Konfino |
| 6,362,161 | B1 | 3/2002 | Konfino |
| 6,448,225 | B2 | 9/2002 | O'Connor |
| 6,454,746 | B1 | 9/2002 | Bydlon |
| 6,506,410 | B1 | 1/2003 | Park |
| 6,514,938 | B1 | 2/2003 | Gad |
| 6,596,316 | B2 | 7/2003 | Lyons |

(Continued)

FOREIGN PATENT DOCUMENTS

| | | | |
|---|---|---|---|
| AU | 2013203367 | B2 | 6/2015 |
| CA | 2020477 | C | 11/2000 |

(Continued)

OTHER PUBLICATIONS

Fletcher et al., (2002) Copolymer 1 (glatiramer acetate) in relapsing forms of multiple sclerosis: open multicenter study of alternate-day administration. Clin Neuropharmacol 25(1): 11-15.

Ford et al., (2006) A prospective open-label study of glatiramer acetate: over a decade of continuous use in multiple sclerosis patients. Mult Scler 12(3): 309-320.

Franklin M and Franz DN; Drug Absorption, Action, and Disposition. In Remington: The Science and Practice of Pharmacy. Paul Beringer ed., 21st edition (2005). Lippincott Williams & Wilkins. pp. 1142-1170, 1167.

Frenken et al., (1994) Analysis of the efficacy of measures to reduce pain after subcutaneous administration of epoetin alfa. Nephrol Dial Transplant 9(9): 1295-1298.

Frick and Pfenniger; Serono to sell Amgen multiple sclerosis drug [Novantrone] in U.S., Firstword Pharma (Nov. 13, 2002), retrieved on May 27, 2015. http://bit.ly/1QXqhpR.

(Continued)

*Primary Examiner* — Alan D Diamond
(74) *Attorney, Agent, or Firm* — The Webb Law Firm

(57) ABSTRACT

Long acting parenteral pharmaceutical compositions comprising a therapeutically effective amount of glatiramer are provided. In particular, the present invention provides a long acting pharmaceutical composition comprising a therapeutically effective amount of glatiramer acetate in depot form suitable for administering at a medically acceptable location in a subject in need thereof. The depot form is suitable for subcutaneous or intramuscular implantation or injection.

23 Claims, 9 Drawing Sheets

(56) References Cited

U.S. PATENT DOCUMENTS

| | | | |
|---|---|---|---|
| 6,620,847 | B2 | 9/2003 | Konfino |
| 6,800,285 | B2 | 10/2004 | Rodriguez |
| 6,800,287 | B2 | 10/2004 | Gad |
| 6,835,711 | B2 | 12/2004 | Eisenbach-Schwartz |
| 6,844,314 | B2 | 1/2005 | Eisenbach-Schwartz |
| 6,861,064 | B1 | 3/2005 | Laakso |
| 6,939,539 | B2 | 9/2005 | Konfino |
| 7,022,663 | B2 | 4/2006 | Gilbert |
| 7,033,582 | B2 | 4/2006 | Yong |
| 7,074,580 | B2 | 7/2006 | Gad |
| 7,163,802 | B2 | 1/2007 | Gad |
| 7,195,778 | B2 | 3/2007 | Fleshner-Barak |
| 7,199,098 | B2 | 4/2007 | Konfino |
| 7,230,085 | B2 | 6/2007 | Griffiths |
| 7,279,172 | B2 | 10/2007 | Aharoni |
| 7,351,686 | B2 | 4/2008 | Eisenbach-Schwartz |
| 7,381,790 | B2 | 6/2008 | Strominger |
| 7,425,332 | B2 | 9/2008 | Sela |
| 7,429,374 | B2 | 9/2008 | Klinger |
| 7,495,072 | B2 | 2/2009 | Dolitzky |
| 7,560,100 | B2 | 7/2009 | Pinchasi |
| 7,576,051 | B2 | 8/2009 | Kurokawa |
| 7,615,359 | B2 | 11/2009 | Gad |
| 7,625,861 | B2 | 12/2009 | Konfino |
| 7,635,695 | B2 | 12/2009 | Burkitt |
| 7,655,221 | B2 | 2/2010 | Rasmussen |
| 7,834,039 | B2 | 11/2010 | Hobson |
| 7,855,176 | B1 | 12/2010 | Altman |
| 7,923,215 | B2 | 4/2011 | Klinger |
| 7,928,131 | B2 | 4/2011 | Buzard |
| 7,968,511 | B2 | 6/2011 | Vollmer |
| 8,008,258 | B2 | 8/2011 | Aharoni |
| 8,138,201 | B2 | 3/2012 | Kalafer |
| 8,232,250 | B2 | 7/2012 | Klinger |
| 8,236,778 | B2 | 8/2012 | Avila Zaragoza |
| 8,367,605 | B2 | 2/2013 | Konfino |
| 8,389,228 | B2 | 3/2013 | Klinger |
| 8,399,211 | B2 | 3/2013 | Gad |
| 8,399,413 | B2 | 3/2013 | Klinger |
| 8,440,622 | B2 | 5/2013 | Stossel |
| 8,709,433 | B2 | 4/2014 | Kasper |
| 8,759,302 | B2 | 6/2014 | Dhib-Jalbut |
| 8,815,511 | B2 | 8/2014 | Tchelet |
| 8,920,373 | B2 | 12/2014 | Altman |
| 8,969,302 | B2 | 3/2015 | Klinger |
| 9,018,170 | B2 | 4/2015 | Altman |
| 9,155,775 | B1 | 10/2015 | Cohen |
| 9,155,776 | B2 | 10/2015 | Klinger |
| 9,402,874 | B2 | 8/2016 | Klinger |
| 9,702,007 | B2 | 7/2017 | Tchelet |
| 11,167,003 | B2 * | 11/2021 | Danon ..... A61P 25/00 |
| RE49,251 | E * | 10/2022 | Marom ..... A61K 9/1647 |
| 2001/0007758 | A1 | 7/2001 | Weiner |
| 2002/0037848 | A1 | 3/2002 | Eisenbach-Schwartz |
| 2002/0077278 | A1 | 6/2002 | Yong |
| 2002/0137681 | A1 | 9/2002 | Steinman |
| 2003/0092059 | A1 | 5/2003 | Salfeld |
| 2003/0104048 | A1 | 6/2003 | Patel |
| 2003/0144286 | A1 | 7/2003 | Frenkel |
| 2004/0038887 | A1 | 2/2004 | Strominger |
| 2004/0106554 | A1 | 6/2004 | Konfino |
| 2005/0014694 | A1 | 1/2005 | Yong |
| 2005/0019322 | A1 | 1/2005 | Rodriguez |
| 2005/0170004 | A1 | 8/2005 | Rosenberger |
| 2005/0170005 | A1 | 8/2005 | Rashba-Step |
| 2005/0171286 | A1 | 8/2005 | Konfino |
| 2005/0277885 | A1 | 12/2005 | Scherer |
| 2006/0154862 | A1 | 7/2006 | Ray |
| 2006/0172942 | A1 | 8/2006 | Dolitzky |
| 2006/0189527 | A1 | 8/2006 | Rasmussen |
| 2006/0194725 | A1 | 8/2006 | Rasmussen |
| 2006/0240463 | A1 | 10/2006 | Lancet |
| 2006/0264354 | A1 | 11/2006 | Aharoni |
| 2006/0276390 | A1 * | 12/2006 | Aharoni et al. ..... 514/12 |
| 2007/0021324 | A1 | 1/2007 | Dolitzky |
| 2007/0021341 | A1 | 1/2007 | Sela |
| 2007/0037740 | A1 | 2/2007 | Pinchasi |
| 2007/0048794 | A1 | 3/2007 | Gad |
| 2007/0054857 | A1 | 3/2007 | Pinchasi |
| 2007/0059798 | A1 | 3/2007 | Gad |
| 2007/0081976 | A1 | 4/2007 | Cohen |
| 2007/0135466 | A1 | 6/2007 | Ledeboer |
| 2007/0161566 | A1 | 7/2007 | Pinchasi |
| 2007/0173442 | A1 | 7/2007 | Vollmer |
| 2007/0244056 | A1 | 10/2007 | Hayardeny |
| 2007/0248569 | A1 | 10/2007 | Eisenbach-Schwartz |
| 2008/0063687 | A1 | 3/2008 | Chou |
| 2008/0085269 | A1 | 4/2008 | Eisenbach-Schwartz |
| 2008/0118553 | A1 | 5/2008 | Frenkel |
| 2008/0194462 | A1 | 8/2008 | Wucherpfennig |
| 2008/0207526 | A1 | 8/2008 | Strominger |
| 2008/0248122 | A1 | 10/2008 | Rashba-Step |
| 2008/0261894 | A1 | 10/2008 | Kreitman |
| 2008/0279819 | A1 | 11/2008 | Went |
| 2009/0048181 | A1 | 2/2009 | Schipper |
| 2009/0053253 | A1 | 2/2009 | Klinger |
| 2009/0118298 | A1 | 5/2009 | George |
| 2009/0130121 | A1 | 5/2009 | Arnon |
| 2009/0149541 | A1 | 6/2009 | Stark |
| 2009/0191173 | A1 | 7/2009 | Eisenbach-Schwartz |
| 2009/0237078 | A1 | 9/2009 | Shriver |
| 2010/0135953 | A1 | 6/2010 | Eisenbach-Schwartz |
| 2010/0160894 | A1 | 6/2010 | Julian |
| 2010/0167983 | A1 | 7/2010 | Kreitman |
| 2010/0210817 | A1 | 8/2010 | Gad |
| 2010/0226963 | A1 | 9/2010 | Cooper |
| 2010/0285600 | A1 | 11/2010 | Lancet |
| 2010/0298227 | A1 | 11/2010 | Aharoni |
| 2010/0305023 | A1 | 12/2010 | Stark |
| 2011/0046065 | A1 | 2/2011 | Klinger |
| 2011/0060279 | A1 | 3/2011 | Altman |
| 2011/0066112 | A1 | 3/2011 | Altman |
| 2012/0015891 | A1 | 1/2012 | Marom |
| 2012/0027718 | A1 | 2/2012 | Kreitman |
| 2012/0309671 | A1 | 12/2012 | Klinger |
| 2013/0165387 | A1 | 6/2013 | Klinger |
| 2014/0107208 | A1 | 4/2014 | Comabella |
| 2014/0193827 | A1 | 7/2014 | Schwartz |
| 2014/0271532 | A1 | 9/2014 | Kreitman |
| 2014/0271630 | A1 | 9/2014 | Vollmer |
| 2014/0294899 | A1 | 10/2014 | Kasper |
| 2014/0322158 | A1 | 10/2014 | Dhib-Jalbut |
| 2015/0045306 | A1 | 2/2015 | Tchelet |
| 2015/0164977 | A1 | 6/2015 | Klinger |
| 2016/0250251 | A1 | 9/2016 | Klinger |

FOREIGN PATENT DOCUMENTS

| | | | |
|---|---|---|---|
| CN | 1398584 | A | 2/2003 |
| EP | 1799703 | B1 | 1/2010 |
| JP | H01121222 | A | 5/1989 |
| JP | 2002-500631 | A | 1/2002 |
| JP | 2007-500693 | A | 1/2007 |
| JP | 2007-509981 | A | 4/2007 |
| JP | 2007-517902 | A | 7/2007 |
| JP | 2007-531701 | A | 11/2007 |
| JP | 2009-515999 | A | 4/2009 |
| WO | 95/31990 | | 11/1995 |
| WO | 95031990 | A1 | 11/1995 |
| WO | 97026869 | A1 | 7/1997 |
| WO | 98030227 | A1 | 7/1998 |
| WO | 00/05250 | | 2/2000 |
| WO | 00005249 | A2 | 2/2000 |
| WO | 0005250 | A1 | 2/2000 |
| WO | 00018794 | A1 | 4/2000 |
| WO | 00020010 | A1 | 4/2000 |
| WO | 00/27417 | | 5/2000 |
| WO | 0027417 | A1 | 5/2000 |
| WO | 01/52878 | | 7/2001 |
| WO | 0152878 | A2 | 7/2001 |
| WO | 01060392 | A1 | 8/2001 |
| WO | 01/93893 | | 12/2001 |
| WO | 0193893 | A2 | 12/2001 |
| WO | 01093828 | A1 | 12/2001 |

(56) References Cited

FOREIGN PATENT DOCUMENTS

| | | | |
|---|---|---|---|
| WO | 01097846 | A1 | 12/2001 |
| WO | 03048735 | A2 | 6/2003 |
| WO | 2004043995 | A2 | 5/2004 |
| WO | 2004064717 | A2 | 8/2004 |
| WO | 2004091573 | A1 | 10/2004 |
| WO | 2004103297 | A2 | 12/2004 |
| WO | 2005009333 | A2 | 2/2005 |
| WO | 2005035088 | A2 | 4/2005 |
| WO | 2005041933 | A1 | 5/2005 |
| WO | 2005070332 | A1 | 8/2005 |
| WO | 2005084377 | A2 | 9/2005 |
| WO | 2005085323 | A2 | 9/2005 |
| WO | 2005120542 | A2 | 12/2005 |
| WO | 2006029036 | A2 | 3/2006 |
| WO | 2006029393 | A2 | 3/2006 |
| WO | 2006029411 | A2 | 3/2006 |
| WO | 2006050122 | A1 | 5/2006 |
| WO | 2006057003 | A2 | 6/2006 |
| WO | 2006083608 | A1 | 8/2006 |
| WO | 2006089164 | A1 | 8/2006 |
| WO | 2006116602 | A2 | 11/2006 |
| WO | 2007021970 | A2 | 2/2007 |
| WO | 2007022254 | A2 | 2/2007 |
| WO | 2007030573 | A2 | 3/2007 |
| WO | 2007059342 | A2 | 5/2007 |
| WO | 2007081975 | A2 | 7/2007 |
| WO | 2008006026 | A1 | 1/2008 |
| WO | 2008/075365 | | 6/2008 |
| WO | 2008075365 | A1 | 6/2008 |
| WO | 2009040814 | A1 | 4/2009 |
| WO | 2009063459 | A2 | 5/2009 |
| WO | 2009070298 | A1 | 6/2009 |
| WO | 2010011879 | A2 | 1/2010 |
| WO | 2011008274 | A2 | 1/2011 |
| WO | 2011022063 | A1 | 2/2011 |
| WO | 2012051106 | A1 | 4/2012 |
| WO | 2012143924 | A1 | 10/2012 |
| WO | 2013055683 | A1 | 4/2013 |
| WO | 2014058976 | A2 | 4/2014 |
| WO | 2014107533 | A2 | 7/2014 |
| WO | 2014165280 | A1 | 10/2014 |

OTHER PUBLICATIONS

Fridkis-Hareli et al., (1999) Binding motifs of copolymer 1 to multiple sclerosis- and rheumatoid arthritis-associated HLA-DR molecules. J Immunol 162(8): 4697-4704.

Friese et al., (2006) The value of animal models for drug development in multiple sclerosis. Brain 129(Pt 8): 1940-1952.

Frohman et al., (2006) Multiple sclerosis—the plaque and its pathogenesis. N Engl J Med 354(9): 942-955.

Gagnon Louise; Every-Other-Day Dosing of Glatiramer Acetate Reduces Adverse Reactions with Comparable Efficacy to Daily Dosing: Presented at WCTRMS, Peerview Press, Sep. 21, 2008, http://www.peerviewpress.com/every-other-day-dosing-glatiramer-acetate-reduces-adverse-reactions-comparable-efficacy-daily-dosing-presented-wctrms (last visited Mar. 8, 2016).

Ge et al., (2000) Glatiramer acetate (Copaxone) treatment in relapsing-remitting MS: quantitative MR assessment. Neurology 54(4): 813-817.

Ghose et al., (2007) Transcutaneous immunization with Clostridium difficile toxoid A induces systemic and mucosal immune responses and toxin A-neutralizing antibodies in mice. Infect Immun 75(6): 2826-2832.

Giancarlo Comi, Forte: Results from a phase II, 1-year, Randomized, Double-blind, Parallel-Group, Dose-Comparison Study with Glatiramer Acetate in Relapsing-Remitting Multiple Sclerosis, Presented at World Congress on Treatment and Research in Multiple Sclerosis: 2008 Joint Meeting of the American, European, and Latin America Committees on Treatment and Research in Multiple Sclerosis, San Raffaele, Italy (Actrims, Ectrims, Lactrims) (2008).

Giuliani et al., (2005) Additive effect of the combination of glatiramer acetate and minocycline in a model of MS. J Neuroimmunol 158(1-2): 213-221.

Gladwell Malcolm; High Prices: How to think about prescription drugs, New Yorker (Oct. 25, 2004), retrieved on Sep. 8, 2012. http://www.newyorker.com/magazine/2004/10/25/high-prices (accessed Feb. 28, 2016).

Glenn et al., (1998) Transcutaneous immunization with cholera toxin protects mice against lethal mucosal toxin challenge. J Immunol 161(7): 3211-3214.

Glenn et al., (2003) Transcutaneous immunization and immunostimulant strategies: capitalizing on the immunocompetence of the skin. Expert Rev Vaccines 2(2): 253-267.

Guideline of Clinical investigation of medicinal products for the treatment of multiple sclerosis EMEA, London Nov. 16, 2006 CPMP/EWP/561/98 Rev. 1, pp. 1-12.

Haines et al., (1998) Linkage of the MHC to familial multiple sclerosis suggests genetic heterogeneity. The Multiple Sclerosis Genetics Group. Hum Mol Genet 7(8): 1229-1234.

Helfand Carly; The top 10 best-selling multiple sclerosis drugs of 2013, Fierce Pharma (Sep. 9, 2014), retrieved on May 27, 2015. http://bit.ly/1UKrDd.

Helfand Carly; Why is Novartis' Copaxone copy lagging? It's all about coverage, analyst explains. Fierce Pharma (Sep. 11, 2015), http://bit.ly/1ia8BNM.

Herper Matthew; Inside The Secret World of Drug Company Rebates. Forbes Pharma & Healthcare (May 10, 2012), http://www.forbes.com/sites/matthewherper/2012/05/10/why-astrazeneca-gives-insurers-60-discounts-on-nexiums-list-price/#155191dd4fd6.

Hestvik et al., (2008) Multiple sclerosis: glatiramer acetate induces anti-inflammatory T cells in the cerebrospinal fluid. Mult Scler 14(6): 749-758.

Hickey (1991) Migration of hematogenous cells through the blood-brain barrier and the initiation of CNS inflammation. Brain Pathol 1(2): 97-105.

Hickey et al., (1991) T-lymphocyte entry into the central nervous system. J Neurosci Res 28(2): 254-260.

Hong et al., (2005) Induction of CD4+CD25+ regulatory T cells by copolymer-I through activation of transcription factor Foxp3. Proc Natl Acad Sci U S A 102(18): 6449-6454.

Hori et al., (2003) Control of regulatory T cell development by the transcription factor Foxp3. Science 299(5609):1057-1061.

Imming et al., (2006) Drugs, their targets and the nature and number of drug targets. Nat Rev Drug Discov 5(10): 821-834 with Corrigenda.

Immunological Responses to Different Doses of Glatiramer Acetate in MS: Analyses from the Forte Trial, Yong W.v., et al., poster session dated Apr. 28, 2009, presented at the 61st Annual American Academy of Neurology meeting in Seattle, Washington U.S.A.

IMS Health; U.S. Pharmaceutical Market: Trends Issues & Outlook (Sep. 15, 2013).

IMS Institute for Health Informatics; Declining Medicine Use and Costs: for Better or Worse?, Chart Notes (May 2013). 56 pages.

IMS Institute for Health Informatics; Medicine Use and Shifting Costs of Healthcare, Chart Notes (Apr. 2014). 59 pages.

In re Copaxone 40 mg Consolidated Cases, No. 14-01171-GMS, Excerpts from Trial Transcript, D.I. Nos. 282-84, 289-92.

In re Copaxone 40 mg Consolidated Cases, No. 14-01171-GMS, Stipulation and [Proposed] Order Concerning Claim Construction Dispute, D.I. 194 (Feb. 12, 2016).

In re Copaxone 40 mg, No. 1:14-cv-01171-CFC (D. Del.), Trial Tr., ECF No. 282-284, 289-292 (discussing Teva's failed GA Depot) (publicly available). 243 pages.

Introduction to Pharmacokinetics and Pharmacodynamics. In: Concepts in Clinical Pharmacokinetics. 5th edition. Edited by DiPiro et al., 2006. American Society of Health-System Pharmacists. pp. 1-17.

Jacobs et al., (2000) Intramuscular interferon beta-1a therapy initiated during a first demyelinating event in multiple sclerosis. Champs Study Group. N Engl J Med 343(13): 898-904.

John J. Jessop, Review and Evaluation of Pharmacology Toxicology Data Original NDA Review (1996) (The 1996 FDA SBOA) (attached as Exhibit A to Exh. 1007).

(56) References Cited

OTHER PUBLICATIONS

Johnson et al., (1998) Extended use of glatiramer acetate (Copaxone) is well tolerated and maintains its clinical effect on multiple sclerosis relapse rate and degree of disability. Copolymer 1 Multiple Sclerosis Study Group. Neurology 50(3): 701-708. Abstract.
Kansara et al., (2009) Subcutaneous Delivery of Small Molecule Formulations: An Insight into Biopharmaceutics & Formulation Strategies. Drug Deliv Technol 9(6): 38-43.
Katz et al., (2004) Successful Desensitization to Glatiramer Acetate (Copaxone) in Two Patients with Multiple Sclerosis. abstract No. P156. Annual Meeting of the American College of Allergy, Asthma and Immunology; Nov. 7-12, 2003; New Orleans.
Khan et al. (2008) Randomized, prospective, rater-blinded, four-year, pilot study to compare the effect of daily versus every-other-day glatiramer acetate 20 mg subcutaneous injections in relapsing-remitting multiple sclerosis. Mult Scler 14 (Suppl. 1): S296.
Khan et al., "A phase 3 trial to assess the efficacy and safety of glatiramer acetate injections 40mg administered 3 times a week compared to placebo" Oct. 13, 2012; European Committee for Treatment and Research in Multiple Sclerosis.
Khan et al., (2009) Glatiramer acetate 20mg subcutaneous twice—weekly versus daily injections: results of a pilot, prospective, randomised, and rater-blinded clinical and MRI 2-year study in relapsing-remitting multiple sclerosis. Multiple Sclerosis 15: S249-S250. Abstract P819.
Khan et al., (2013) Three times weekly glatiramer acetate in relapsing-remitting multiple sclerosis. Ann Neurol 73(6): 705-713.
Klauer and Zettl (2008) Compliance, adherence and the treatment of multiple sclerosis. J Neurol 255 Suppl 6: 87-92.
Kleiner et al., (2010) Immunological Response to Glatiramer Acetate in MS Patients after Different Pretreatments—The CopImmunoNet Study. Neurology 74 (Suppl 2): A554, abstract P06.178.
Kragt et al., (2006) How similar are commonly combined criteria for EDSS progression in multiple sclerosis? Mult Scler 12(6): 782-786.
Lambert and Laurent (2008) Intradermal vaccine delivery: will new delivery systems transform vaccine administration? Vaccine 26(26): 3197-3208.
Lando et al., (1979) Effect of cyclophosphamide on suppressor cell activity in mice unresponsive to EAE. J Immunol 123(5): 2156-2160.
LeBano Lauren (2012) Gray Matter Atrophy May Serve as an Effective Outcome measure for MS Clinical Trials. Neurology Reviews 20(2): 8. 5 pages.
Abramsky et al., (1982) Alpha-fetoprotein suppresses experimental allergic encephalomyelitis. J Neuroimmunol 2(1): 1-7.
Aharoni et al., (1998) Bystander suppression of experimental autoimmune encephalomyelitis by T cell lines and clones of the Th2 type induced by copolymer 1. J. Neuroimmunol. 91(1-2): 135-146.
Aharoni et al., (2005) The immunomodulator glatiramer acetate augments the expression of neurotrophic factors in brains of experimental autoimmune encephalomyelitis mice. Proc Natl Acad Sci USA 102(52): 19045-19050.
Armstrong et al., (1997) A novel synthesis of disubstituted ureas using titanium (IV) isopropoxide and sodium borohydride. Tetrahedron Letters 38(9): 1531-1532.
Artuso et al., (2007) Preparation of mono-, di-, and trisubstituted ureas by carbonylation of aliphatic amines with S,S-dimethyl dithiocarbonate. Synthesis 22: 3497-3506.
Ben-Nun et al., (1996) The autoimmune reactivity to myelin oligodendrocyte glycoprotein (MOG) in multiple sclerosis is potentially pathogenic: effect of copolymer 1 on MOG-induced disease. J Neurol 243(4 Suppl 1): S14-S22.
Bolton et al., (1982) Immunosuppression by cyclosporin A of experimental allergic encephalomyelitis. J Neurol Sci 56(2-3): 147-153.
Bouissou et al., (2006) The Influence of Surfactant on PLGA Microsphere Glass Transition and Water Sorption: Remodeling the Surface Morphology to Attenuate the Burst Release. Pharmaceutical Research 23(6): 1295-1305.
Bright et al., (1999) Tyrphostin B42 inhibits IL-12-induced tyrosine phosphorylation and activation of Janus kinase-2 and prevents experimental allergic encephalomyelitis. J Immunol 162(10): 6255-6262.
Brown (2005) Commercial challenges of protein drug delivery. Expert Opinion on Drug Delivery, Informa Healthcare, GB 2(1): 29-42.
Cohen et al., (2007) Randomized, double-blind, dose-comparison study of glatiramer acetate in relapsing-remitting MS. Neurology 68(12): 939-944.
Fridkis-Hareli et al., (1999) Binding of random copolymers of three amino acids to class II MHC molecules. Int Immunol 11(5): 635-641.
Goodson JM: Dental applications; in Langer LS, Wise DL (eds): Medical Applications of Controlled Release. Boca Raton, CRC Press, 1984, vol. 2, pp. 115-138.
Johnson et al., (1995) Copolymer 1 reduces relapse rate and improves disability in relapsing-remitting multiple sclerosis. Results of a phase III multicenter, double-blind, placebo-controlled trial. Neurology 45(7): 1268-1276.
Langer (1990) Science, American Association for the Advancement of Science, US 249(4976): 1527-1533.
Shenoy et al., (2002) Poly(DL-lactide-co-glycolide) microporous microsphere-based depot formulation of a peptide-like antineoplastic agent. J Microencapsul 19(4): 523-535.
Sorensen et al., (1998) Intravenous immunoglobulin G reduces MRI activity in relapsing multiple sclerosis. Neurology 50(5): 1273-1281.
Stern et al., (2008) Amino acid copolymer-specific IL-10-secreting regulatory T cells that ameliorate autoimmune diseases in mice. Proc Natl Acad Sci USA 105(13): 5172-5176.
Teitelbaum et al., (1971) Suppression of experimental allergic encephalomyelitis by a synthetic polypeptide. Eur J Immunol 1(4): 242-248.
Teitelbaum et al., (1973) Suppression by several synthetic polypeptides of experimental allergic encephalomyelitis induced in guinea pigs and rabbits with bovine and human basic encephalitogen. Eur J Immunol 3(5): 273-279.
Teitelbaum et al., (1974) Suppression of experimental allergic encephalomyelitis in rhesus monkeys by a synthetic basic copolymer. Clin. Immunol. Immunopathol 3(2): 256-262.
Teitelbaum et al., (1996) Copolymer 1 inhibits chronic relapsing experimental allergic encephalomyelitis induced by proteolipid protein (PLP) peptides in mice and interferes with PLP-specific T cell responses. J Neuroimmunol 64(2): 209-217.
Webb et al., (1973) Correlation between strain differences in susceptibility to experimental allergic encephalomyelitis and the immune response to encephalitogenic protein in inbred guinea pigs. Immunol Commun 2(2): 185-192.
ISR of PCT/IL2010/000679 mailed Dec. 27, 2010.
ISR of PCT/IL2012/050138 mailed Aug. 31, 2012.
Castells (2009) Rapid desensitization for hypersensitivity reactions to medications. Immunol Allergy Clin North Am 29 (3): 585-606.
Chabot et al., (2002) Cytokine production in T lymphocyte-microglia interaction is attenuated by glatiramer acetate: a mechanism for therapeutic efficacy in multiple sclerosis. Mult Scler 8(4): 299-306.
Chantelau et al., (1991) What makes insulin injections painful? BMJ 303(6793): 26-27.
Chapter 8: Drug elimination and pharmacokinetics. pp. 106-119. H.P. Pharmacology (5th ed. 2005); edited by Rang HP, Dale MM, Ritter JM and Moore PK.
Chen et al., (1991) Mu receptor binding of some commonly used opioids and their metabolites. Life Sci 48(22): 2165-2171.
Chen et al., (2002) Sustained immunological effects of Glatiramer acetate in patients with multiple sclerosis treated for over 6 years. J Neurol Sci 201(1-2): 71-77.
Cohen et al., (2012) Alemtuzumab versus interferon beta 1a as first-line treatment for patients with relapsing-remitting multiple sclerosis: a randomised controlled phase 3 trial. Lancet 380(9856): 1819-1828.
Comi and Moiola (2002) Glatiramer acetate. Neurologia 17(5): 244-258.

(56) References Cited

OTHER PUBLICATIONS

Comi et al., (2001) European/Canadian multicenter, double-blind, randomized, placebo-controlled study of the effects of glatiramer acetate on magnetic resonance imaging—measured disease activity and burden in patients with relapsing multiple sclerosis. European/Canadian Glatiramer Acetate Study Group. Ann Neurol 49(3): 290-297.
Comi et al., (2008) Results from a phase III, 1-year, Randomized, Double-blind, Parallel-Group, Dose-Comparison Study with Glatiramer Acetate in Relapsing-Remitting Multiple Sclerosis. Mult Scler 14: S299-S301.
Comi et al., (2009) Effect of glatiramer acetate on conversion to clinically definite multiple sclerosis in patients with clinically isolated syndrome (PreCISe study): a randomised, double-blind, placebo-controlled trial. Lancet 374(9700): 1503-1511.
Comi G. "Treatment with glatiramer acetate delays conversion to clinically definite multiple sclerosis (CDMS) in patients with clinically isolated syndromes (CIS)". Program and abstracts of the American Academy of Neurology 60th Annual Meeting; Apr. 12-19, 2008; Chicago, Illinois. LBS.003.
Conner (2014) Glatiramer acetate and therapeutic peptide vaccines for multiple sclerosis. Journal of Autoimmunity and Cell Responses 1: Article 3; 11 pages.
Copaxone 20 mg/ml or Copaxone 40 mg/ml, NDA 020622/S-089 FDA Approved Labeling Text dated Jan. 28, 2014.
Copaxone 20 mg/ml, Solution for Injection, Pre-Filled Syringe, Summary of Product Characteristics updated on Apr. 17, 2009.
Copaxone Prescribing Information (Jan. 2014). 8 pages.
Copaxone, https://scamparoo.wordpress.com/2008/04/11/mstherapies-copaxone/ (dated Apr. 11, 2008 (accessed Feb. 5, 2015)).
Copaxone® U.S. Product Label (2001).
Copaxone® U.S. Product Label (Feb. 2009).
Copaxone®, Food and Drug Administration Approved Labeling, Jan. 2014, submitted as Exhibit 1057 in Inter Partes Review Case No. IPR2015-00643.
Copaxone®, Physicians' Desk Reference, 62nd ed. Montvale, NJ, Thomson Healthcare Inc., pp. 3231-3235 (2008).
Costello et al., (2008) Recognizing nonadherence in patients with multiple sclerosis and maintaining treatment adherence in the long term. Medscape J Med 10(9): 225.
David J and Stewart MB; Commercial Success: Economic Principles Applied to Patent Litigation. In: Economic Damages in Intellectual Property: A Hands-On Guide to Litigation. Edited by Slottje D. John Wiley & Sons, Inc. 2006. pp. 159-170.
De Stefano et al., (2009) The results of two multicenter, open-label studies assessing efficacy, tolerability and safety of protiramer, a high molecular weight synthetic copolymeric mixture, in patients with relapsing-remitting multiple sclerosis. Mult Scler 15(2): 238-243.
De Stefano et al., (2010) Assessing brain atrophy rates in a large population of untreated multiple sclerosis subtypes. Neurology 74(23): 1868-1876.
de Vijlder (2003) Primary congenital hypothyroidism: defects in iodine pathways. Eur J Endocrinol 149(4): 247-256.
Devonshire et al., (2006) The Global Adherence Project—A multicentre observational study on adherence to disease-modifying therapies in patients suffering from relapsing-remitting multiple sclerosis, Multiple Sclerosis 12: S1 (P316).
Dhib-Jalbut (2002) Mechanisms of action of interferons and glatiramer acetate in multiple sclerosis. Neurology 58(8 Suppl 4): S3-S9.
Dhib-Jalbut (2003) Glatiramer acetate (Copaxone) therapy for multiple sclerosis. Pharmacol Ther 98(2): 245-255. Abstract.
DiPiro et al., Introduction to pharmacokinetics and pharmacodynamics. In: Concepts in Clinical Pharmacodynamics (5th ed. 2010). pp. 1-17.
Duda et al., (2000) Glatiramer acetate (Copaxone®) induces degenerate, Th2-polarized immune responses in patients with multiple sclerosis. J Clin Invest 105(7): 967-976.
Edgar et al., (2004) Lipoatrophy in patients with multiple sclerosis on glatiramer acetate. Can J Neurol Sci 31(1): 58-63.
Efimova et al., (2005) Changes in the secondary structure of proteins labeled with 125I: CD spectroscopy and enzymatic activity studies. Journal of Radioanalytical and Nuclear Chemistry 264(1): 91-96.
Extavia® Product Label (2009). Prescribing information.
Extavia®, Abbreviated Drug Monograph: Interferon beta 1b (Extavia®), Sep. 2010, submitted as Exhibit 1053 in Inter Partes Review Case Nos. IPR2015-00643, IPR2015-00644 and IPR2015-00830.
Farina et al., (2001) Treatment of multiple sclerosis with Copaxone (COP): Elispot assay detects COP-induced interleukin-4 and interferon-gamma response in blood cells. Brain 124(Pt 4): 705-719.
FDA approves new MS treatment regimen developed at Wayne State University by Dr. Omar Khan, Division of Research—Research@Wayne, https://research.wayne.edu/rwnews/article.php?id=1319 (Posted on: Thursday, Jan. 30, 2014; last visited Mar. 8, 2016).
FDA Guidance for Industry—Population Pharmacokinetics (1999). 35 pages.
FDA Guidance for Industry—Statistical Approaches to Establishing Bioequivalence (2001). 48 pages.
FDA, Guideline for Industry: Dose-Response Information to Support Drug Registration (1994).
Figure: Perception of 3-times-a-week Copaxone 40mg compared to Daily Copaxone 20mg. 2015.
Figure: Perceptions of Copaxone® 40mg compared to Daily Generic GA. 2015.
Figure: Perceptions of Copaxone® 40mg vs. 20mg. 2015.
Figure: Rationale for Discussing 20mg and 40mg for First Line Patients. 2015.
Figure: Rationale for Requesting Copaxone. 2015.
Filippi et al., (2006) Effects of oral glatiramer acetate on clinical and MRI-monitored disease activity in patients with relapsing multiple sclerosis: a multicentre, double-blind, randomised, placebo-controlled study. Lancet Neurol, http://neurology.thelancet.com. Published online Jan. 20, 2006 DOI:10.1016/S1474-4422(06)70327-1. 8 pages.
Filippi et al., (2010) The contribution of MRI in assessing cognitive impairment in multiple sclerosis. Neurology 75(23): 2121-2128.
Fisher et al., (2008) Gray matter atrophy in multiple sclerosis: a longitudinal study. Ann Neurol 64(3): 255-265.
Fisniku et al., (2008) Gray matter atrophy is related to long-term disability in multiple sclerosis. Ann Neurol 64(3): 247-254.
Flechter et al., (2002) Comparison of glatiramer acetate (Copaxone) and interferon β-1b (Betaferon) in multiple sclerosis patients: an open-label 2-year follow-up. J Neurol Sci 197(1-2): 51-55.
Bala et al., PLGA nanoparticles in drug delivery: the state of the art. Critical Reviews™ in Therapeutic Drug Carrier Systems, 2004, pp. 387-422, vol. 21, No. 5.
Weber et al., (2004) Multiple sclerosis: glatiramer acetate inhibits monocyte reactivity in vitro and in vivo. Brain 127(Pt 6): 1370-1378.
Weber et al., (2007) Mechanism of action of glatiramer acetate in treatment of multiple sclerosis. Neurotherapeutics 4(4): 647-653.
Webster's Ninth New Collegiate Dictionary, Merriam-Webster, Inc., 1985, p. 872, submitted as Exhibit 2027 in Inter Partes Review Case No. IPR2015-00830.
Wekerle et al., (1986) Cellular immune reactivity within the CNS. Trends in Neurosciences 9: 271-277.
Wolinsky (2004) Glatiramer acetate for the treatment of multiple sclerosis. Expert Opin Pharmacother 5(4): 875-891.
Wolinsky (2006) The use of glatiramer acetate in the treatment of multiple sclerosis. Adv Neurol 98: 273-292. Abstract.
Wolinsky et al., (2007) Glatiramer acetate in primary progressive multiple sclerosis: results of a multinational, multicenter, double-blind, placebo-controlled trial. Ann Neurol 61(1): 14-24.
Wolinsky et al., (2015) Glacier: An open-label, randomized, multicenter study to assess the safety and tolerability of glatiramer acetate 40 mg three-times weekly versus 20 mg daily in patients with relapsing-remitting multiple sclerosis. Mult Scler Relat Disord 4(4): 370-376.
Wroblewski (1991) Mechanism of deiodination of 125I-human growth hormone in vivo. Relevance to the study of protein disposition. Biochem Pharmacol 42(4): 889-897.

(56) References Cited

OTHER PUBLICATIONS

Wynn et.al., Patient Experience with Glatiramer Acetate 40 mg/1 ml Three-Times Weekly Treatment for Relapsing-Remitting Multiple Sclerosis: Results from the Glacier Extension Study. Neurology 84 (14 Supplement): P7.218. Presented at The 8th Congress of the Pan-Asian Committee for Treatment and Research in Multiple Sclerosis, Seoul, Republic of Korea (Nov. 19-21, 2015).
Yong (2002) Differential mechanisms of action of interferon-beta and glatiramer aetate in MS. Neurology 59(6): 802-808.
Zellner et al., (2005) Quantitative validation of different protein precipitation methods in proteome analysis of blood platelets. Electrophoresis 26(12): 2481-2489.
Zhang and Hay (2014a) Cost-effectiveness of Fingolimod, Teriflunomide, Dimethyl Fumarate and Intramuscular Interferon Beta-1a in Relapsing-remitting Multiple Sclerosis. Poster, Monday Morning, PND20, ISPOR 19th Annual International Conference, May 2014, Montreal, Quebec, Canada.
Zhang and Hay (2014b) Cost-effectiveness of Fingolimod, Teriflunomide, Dimethyl Fumarate and Intramuscular Interferon Beta-1a in Relapsing-remitting Multiple Sclerosis. American Society for Health Economics 5th Biennial Conference, Jun. 2014, Los Angeles, CA.
Zhang et al., (2015) Cost effectiveness of fingolimod, teriflunomide, dimethyl fumarate and intramuscular interferon-31a in relapsing-remitting multiple sclerosis. CNS Drugs 29(1): 71-81.
Ziemssen (2005) Modulating processes within the central nervous system is central to therapeutic control of multiple sclerosis. J Neurol 252 Suppl 5: v38-v45.
Ziemssen and Gilgun-Sherki (2015) Sub-analysis of geographical variations in the 2-year observational Coptimize trial of patients with relapsing-remitting multiple sclerosis converting to glatiramer acetate. BMC Neurol 15: 189.
Ziemssen and Schrempf (2007) Glatiramer acetate: mechanisms of action in multiple sclerosis. Int Rev Neurobiol 79: 537-570.
Ziemssen et al., (2001) Risk-benefit assessment of glatiramer acetate in multiple sclerosis. Drug Saf 24(13): 979-990.
Ziemssen et al., (2002) Glatiramer acetate-specific T-helper 1- and 2-type cell lines produce BDNF: implications for multiple sclerosis therapy. Brain-derived neurotrophic factor. Brain 125(Pt 11): 2381-2391.
Ziemssen et al., (2008) Effects of glatiramer acetate on fatigue and days of absence from work in first-time treated relapsing-remitting multiple sclerosis. Health Qual Life Outcomes 6: 67.
Ziemssen et al., (2008) Presence of Glatiramer Acetate-Specific TH2 Cells in the Cerebrospinal Fluid of Patients with Multiple Sclerosis 12 Months After the Start of Therapy with Glatiramer Acetate, J Neurodegen Regen 1: 19-22.
Ziemssen et al., (2014) A 2-year observational study of patients with relapsing-remitting multiple sclerosis converting to glatiramer acetate from other disease-modifying therapies: the Coptimize trial. J Neurol 261(11): 2101-2111.
Ziemssen et al., (2014) QualiCOP: An Open-Label, Prospective, Observational Study of Glatiramer Acetate in Patients with Relapsing-Remitting Multiple Sclerosis. Retrieved form: http://www.comtecmed.com/cony/2014/Uploads/Editor/Rainer.pdf.
Ziemssen T. (2004) Neuroprotection and Glatiramer Acetate: The Possible Role in the Treatment of Multiple Sclerosis. In: Vécsei L. (eds) Frontiers in Clinical Neuroscience. Advances in Experimental Medicine and Biology, vol. 541., pp. 111-134. Springer, Boston, MA. https://doi.org/10.1007/978-1-4419-8969-7_7.
Zivadinov et al., (2008) Mechanisms of action of disease-modifying agents and brain volume changes in multiple sclerosis. Neurology 71(2): 136-144.
Zivadinov et al., (2015) MRI indicators of brain tissue loss: 3-year results of the Glatiramer Acetate Low-frequency Administration (Gala) open-label extension study in relapsing-remitting multiple sclerosis (P7.255). Neurology 84 (14 Supplement): P7.255. Presented at The American Academy of Neurology 2015 Annual Meeting, Washington, DC (Apr. 18-25, 2015).
"Teva to Present Positive Data for Glatiramer Acetate 40 mg/1ml Given Three Times Weekly for Relapsing-Remitting MS" [online] Teva Pharmaceutical Industries Ltd. Oct. 10, 2012 [retrieved on Apr. 2, 2013]. Retrieved from the Internet: <URL: www.tevapharm.com/Media/News/Pages/2012/1743500.aspx?year=2012&page>.
1996 FDA Meeting Agenda minutes from the Peripheral and Central Nervous System Drug Advisory Committee (dated Sep. 19, 1996) (Exhibit A to Exhibit 1019).
3-Times-A-Week Copaxone® 40 MG, Teva. Retrieved from: https://www.copaxone.com/about-copaxone/copaxone-40-mg on Mar. 10, 2016.
A Multinational, Multicenter, Randomized, Double-Blind, Placebo-Controlled, Parallel-Group Study to Assess the Efficacy, Tolerability and Safety of 40 mg Glatiramer Acetate Injection in Subjects with Amyotrophic Lateral Sclerosis. Protocol ALS-GA-201 (GoALS); Eudract No. 2006-001688-49. Summary of Clinical Trial Results; Jul. 2008. Publication date: Feb. 9, 2018 Retrieved from: https://www.clinicaltrialsregister.eu/ctr-search/trial/2006-001688-49/GB; 62 pages.
A Pilot, Multi-Center, Open-Label, One-Group Study to Explore the Efficacy, Tolerability and Safety of an Oral Once-daily 600 mg Dose of Glatiramer Acetate (GA) in Subjects with Relapsing Remitting (R-R) Multiple Sclerosis (MS). Protocol GA/7026; EudraCT No. 2004-000463-94. Study Conducted (Sep. 2004-Mar. 2006). Summary of Results; Feb. 2007. Publication date: Jan. 4, 2017. Retrieved from: https://www.clinicaltrialsregister.eu/ctr-search/trial/2004-000463-94/results; 25 pages.
A Study to Test the Effectiveness and Safety of a New Higher 40mg Dose of Copaxone® Compared to Copaxone® 20mg, the Currently Approved Dose [online]. ClinicalTrials.gov, 1993 [retrieved on Feb. 13, 2015]. Retrieved from the Internet: <URL: clinicaltrials.gov/show/NCT00202982>; 6 pages.
A to Z of MS Alemtuzumab (Lemtrada), Multiple Sclerosis Trust, retrieved on Jun. 2, 2015. http://bit.ly/1YnlfHQ.
Abramsky et al., (1977) Effect of a synthetic polypeptide (COP 1) on patients with multiple sclerosis and with acute disseminated encephalomeylitis. Preliminary report. J Neurol Sci 31(3): 433-438.
Aharoni (2013) The mechanism of action of glatiramer acetate in multiple sclerosis and beyond. Autoimmun Rev 12(5): 543-553.
Aharoni et al., (1997) Copolymer 1 induces T cells of the T helper type 2 that crossreact with myelin basic protein and suppress experimental autoimmune encephalomyelitis. Proc Natl Acad Sci U S A 94(20): 10821-10826.
Aharoni et al., (2000) Specific Th2 cells accumulate in the central nervous system of mice protected against experimental autoimmune encephalomyelitis by copolymer 1. Proc Natl Acad Sci U S A 97(21): 11472-11477.
Aharoni et al., (2003) Glatiramer acetate-specific T cells in the brain express T helper 2/3 cytokines and brain-derived neurotrophic factor in situ. Proc Natl Acad Sci U S A 100(24): 14157-14162.
Aharoni et al., (2005) Therapeutic effect of the immunomodulator glatiramer acetate on trinitrobenzene sulfonic acid-induced experimental colitis. Inflamm Bowel Dis 11(2): 106-115.
Alison Palkhivala; Doubling the Dose of Glatiramer Acetate Does Not Increase Efficacy. Medscape Medical News (Sep. 22, 2008). Retrieved on Jan. 6, 2015. 2 pages.
All About MS. Posted by: Thixia | Apr. 11, 2008. Rtrieved from: https://scamparoo.wordpress.com/2008/04/11/ms-therapies-copaxone/ (dated Apr. 11, 2008 (accessed Feb. 5, 2015)).
Ampyra Prescribing Information, Acorda Therapeutics (Dec. 2014).
Anand Geeta; Through Charities, Drug Makers Help People—and Themselves, Wall St. J. (Dec. 1, 2005), retrieved on Mar. 8, 2016 http://www.wsj.com/articles/SB113339802749110822.
Anderson et al., (1992) Revised estimate of the prevalence of multiple sclerosis in the United States. Ann Neurol 31(3): 333-336.
Anderson et al., (2010) Injection pain decreases with new 0.5 mL formulation of glatiramer acetate. International Journal of MS Care 12(supp 1): 54. Abstracts from the 24th Annual Meeting of the Consortium of Multiple Sclerosis Centers; Multiple Sclerosis: Sustaining Care, Seeking a Cure, Jun. 2-5, 2010; San Antonio, TX, USA.

(56) References Cited

OTHER PUBLICATIONS

Anderson et al., (2010) Tolerability and safety of novel half milliliter formulation of glatiramer acetate for subcutaneous Injection: an open-label, multicenter, randomized comparative study. J Neurol 257(11): 1917-1923.
Arnon (1996) The development of Cop 1 (Copaxone®), an innovative drug for the treatment of multiple sclerosis: personal reflections. Immunol Lett 50(1-2): 1-15.
Arnon and Aharoni (2004) Mechanism of action of glatiramer acetate in multiple sclerosis and its potential for the development of new applications. Proc Natl Acad Sci U S A 101 Suppl 2(Suppl 2): 14593-14598.
Arnon and Aharoni (2007) Neurogenesis and neuroprotection in the CNS—fundamental elements in the effect of Glatiramer acetate on treatment of autoimmune neurological disorders. Mol Neurobiol 36(3): 245-253.
Avonex® Product Label (2006).
Bains et al., (2010) Glatiramer acetate: successful desensitization for treatment of multiple sclerosis. Ann Allergy Asthma Immunol 104(4): 321-325.
Bakshi et al., (2005) Imaging of multiple sclerosis: role in neurotherapeutics. NeuroRx 2(2): 277-303.
Bartus et al., (1998) Sustained delivery of proteins for novel therapeutic products. Science 281(5380): 1161-1162.
Beer et al., (2011) The prevalence of injection-site reactions with disease-modifying therapies and their effect on adherence in patients with multiple sclerosis: an observational study. BMC Neurol 11: 144.
Benet LZ et al., Pharmacokinetics: The Dynamics of Drug Absorption, Distribution, and Elimination. In: Goodman & Gilman's The Pharmacological Basis of Therapeutics, 9th edition. McGraw-Hill, 1996. pp. 3-27.
Beringer P and Winter ME; Clinical Pharmacokinetics and Pharmacodynamics. In Remington: The Science and Practice of Pharmacy. Paul Beringer ed., 21st edition (2005). Lippincott Williams & Wilkins. pp. 1191-1205, 1197, 1201.
Bermel and Bakshi (2006) The measurement and clinical relevance of brain atrophy in multiple sclerosis. Lancet Neurol 5(2): 158-170.
Berndt et al., (1995) Information, marketing, and pricing in the U.S. antiulcer drug market. Am Econ Rev 85(2): 100-105.
Berndt et al., (2002) An analysis of the diffusion of new antidepressants: variety, quality, and marketing efforts. J Ment Health Policy Econ 5(1): 3-19.
Betaseron® Product Label (Oct. 2003).
Bjartmar and Fox (2002) Pathological mechanisms and disease progression of multiple sclerosis: therapeutic implications. Drugs Today (Barc) 38(1): 17-29.
Blanco et al., (2006) Effect of glatiramer acetate (Copaxone®) on the immunophenotypic and cytokine profile and BDNF production in multiple sclerosis: a longitudinal study. Neurosci Lett 406(3): 270-275.
Boissel and Nony (2002) Using pharmacokinetic-pharmacodynamic relationships to predict the effect of poor compliance. Clin Pharmacokinet 41(1): 1-6.
Bornstein et al., "Treatment of Multiple Sclerosis with Copolymer 1" in Treatment of Multiple Sclerosis: Trial Design, Results and Future Perspectives (Rudick R.A. & Good kin D. E., eds., Springer Lerlag, London, 1992) 173-198. Abstract.
Bornstein et al., "Clinical Trials of a Synthetic Polypeptide (Copolymer 1) for the treatment of Mutliple Sclerosis". In: Gonsett et al., Immunological and Clinical Aspects of Multiple Sclerosis (MTP Press, The Hague, 1984), pp. 144-150. Abstract.
Bornstein et al., (1980) Treatment of multiple sclerosis with a synthetic polypeptide: preliminary results. Trans Am Neurol Assoc 105: 348-350.
Bornstein et al., (1982) Multiple sclerosis: trial of a synthetic polypeptide. Ann Neurol 11(3): 317-319.
Bornstein et al., (1984) Clinical trials of copolymer I in multiple sclerosis. Ann N Y Acad Sci 436: 366-372.
Bornstein et al., (1987) A pilot trial of COP-1 in exacerbating-remitting multiple sclerosis. N Engl J Med 317(7): 408-414.
Bornstein et al., (1988) Clinical experience with COP-1 in multiple sclerosis. Neurology 38(7 Suppl 2): 66-69. Abstract.
Bornstein et al., (1991) A placebo-controlled, double-blind, randomized, two-center, pilot trial of Cop 1 in chronic progressive multiple sclerosis. Neurology 41(4): 533-539.
Bornstein; Clinical Experience: hopeful prospects in multiple sclerosis:. Hospital Practice (Off. Ed.), 1992, vol. 27, No. 5, pp. L135-158, 141-142, 145-158. 1st page.
Brenner et al., (2001) Humoral and cellular immune responses to Copolymer 1 in multiple sclerosis patients treated with Copaxone. J Neuroimmunol 115(1-2): 152-160.
Brunkow et al., (2001) Disruption of a new forkhead/winged-helix protein, scurfin, results in the fatal lymphoproliferative disorder of the scurfy mouse. Nat Genet 27(1): 68-73.
Burger et al., (2009) Glatiramer acetate increases IL-1 receptor antagonist but decreases T cell-induced IL-1β in human monocytes and multiple sclerosis. Proc Natl Acad Sci U S A 106(11): 4355-4359.
Caon et al., (2009) Randomized, Prospective, Rater-Blinded, Four Year Pilot Study to Compare the Effect of Daily Versus Every Other Day Glatiramer Acetate 20 mg Subcutaneous Injections in RRMS Neurology 72:11(3): A317.
Rebif® U.S. Product Label (2003).
Reinke Thomas; MS Drug Going Generic Without Making Waves, Managed Care (Jun. 2015), http://bit.ly/1KcyXdE.
Rich et al., (2004) Stepped-care approach to treating MS: a managed care treatment algorithm. J Manag Care Pharm 10(3 Suppl B): S26-S32.
Rothwell et al., (1997) Doctors and patients don't agree: cross sectional study of patients' and doctors' perceptions and assessments of disability in multiple sclerosis. BMJ 314(7094): 1580-1583.
Rovaris et al., (2008) Cognitive impairment and structural brain damage in benign multiple sclerosis. Neurology 71(19): 1521-1526.
Rubinchik et al., (1998) Responsiveness of human skin mast cells to repeated activation: an in vitro study. Allergy 53 (1): 14-19.
Ruggieri et al., (2007) Glatiramer acetate in multiple sclerosis: a review. CNS Drug Rev 13(2): 178-191.
Rumrill (2009) Multiple Sclerosis: Medical and Psychosocial Aspects, Etiology, Incidence, and Prevalence. Journal of Vocational Rehabilitation 31(2): 75-82.
Ryan and Majno (1977) Acute inflammation. A review. Am J Pathol 86(1): 183-276.
Sage Journals, Table of Contents, http://msj.sagepub.com/content/14/1_suppl.toc (Sep. 2008).
Schmeisser et al., (2000) Radioiodination of human interferon- α2 interferes with binding of C-terminal specific antibodies. J Immunol Methods 238(1-2): 81-85.
Schrempf and Ziemssen (2007) Glatiramer acetate: mechanisms of action in multiple sclerosis. Autoimmun Rev 6(7): 469-475.
Selection of Injection Volume. In: Pharmaceutical Preformulation and Formulation; A Practical Guide from Candidate Drug Selection to Commercial Dosage Form. 2nd edition, 2009. Edited by Gibson M. informa healthcare, p. 326.
Shalit et al., (1996) Abstract 650, Copolymer-1 (Copaxone®) Induces a Non-Immunologic Activation of Connective Tissue Type Mast Cells, 97 J. Allergy & Clinical Immunology 97(1): part 3 (Peroutka Dep. Ex. 12).
Shaw Gina; Exorbitant Drug Costs May Price Out Patients. The Washington Diplomat (Uploaded: Apr. 27, 2011). Retrieved on Jan. 26, 2016. 3 pages.
Shire et al., (2004) Challenges in the development of high protein concentration formulations. J Pharm Sci 93(6): 1390-1402. Abstract.
Simpson et al., (2002) Glatiramer Acetate—A Review of its use in Relapsing-Remitting Multiple Sclerosis. Adis Drug Evaluation; CNS Drugs 16(12): 825-850.
Simpson et al., (2002) Glatiramer acetate: a review of its use in relapsing-remitting multiple sclerosis. CNS Drugs 16 (12): 825-850.
Singer et al., (2012) Comparative injection-site pain and tolerability of subcutaneous serum-free formulation of interferonβ-1a versus

(56) References Cited

OTHER PUBLICATIONS subcutaneous interferonβ-1b: results of the randomized, multicenter, Phase IIIb Reforms study. BMC Neurol 12: 154.
Soares et al., (2006) Localized panniculitis secondary to subcutaneous glatiramer acetate injections for the treatment of multiple sclerosis: a clinicopathologic and immunohistochemical study. J Am Acad Dermatol 55(6): 968-974.
Sodoyez et al., (1980) 125I-insulin: kinetics of interaction with its receptors and rate of degradation in vivo. Am J Physiol 239(1): E3-E8.
Sorensen et al., (2003) Clinical importance of neutralising antibodies against interferon beta in patients with relapsing-remitting multiple sclerosis. Lancet 362(9391): 1184-1191.
Staton Tracy; Sanofi tags newly OK'd MS drug Lemtrada at $158K, ready to tout head-to-head Rebif data, Fierce Pharma Marketing (Nov. 17, 2014), retrieved on May 27, 2015. http://bit.ly/1QDkTIZ.
Stedman's Medical Dictionary for Health Professions and Nursing; Illustrated 6th edition (2008). Wolter Kluwer; Lippincott Williams & Wilkins. p. 1337.
Stewart and Tran (2012) Injectable multiple sclerosis medications: a patient survey of factors associated with injection-site reactions. Int J MS Care 14(1): 46-53.
Stuart (2004) Clinical management of multiple sclerosis: the treatment paradigm and issues of patient management. J Manag Care Pharm 10(3 Suppl B): S19-S25.
Sumowski et al., (2013) Brain reserve and cognitive reserve in multiple sclerosis: what you've got and how you use it. Neurology 80(24): 2186-2193.
Table: Approval Timeline, Multiple Sclerosis Drugs. 2015.
Teva News Release, Phase III Data Published in Annals of Neurology Show That a Higher Concentration Dose of Glatiramer Acetate Given Three Times a Week Reduced Annualized Relapse Rates in the Treatment of Relapsing-Remitting Multiple Sclerosis (Jul. 1, 2013). Retrieved on May 22, 2015. 6 pages.
Teva News Release; New Study Demonstrated Significant Reduction in Annualized Relapse Rate and Halting of Disability Progression in MS Patients Switching to Copaxone® (Apr. 14, 2011). 5 pages.
Tera Press Release, Teva Reports First Quarter 2015 Results (Apr. 30, 2015).
Teva Provides Update on Forte Trial (Jul. 7, 2008).
Teva Provides Update on Forte Trial (Jul. 7, 2008). 2 pages.
Teva Provides Update on Forte Trial Jerusalem, Israel (Jul. 7, 2008).
Teva's Shared Solutions® How to Prepare for Your Injection, http://www.copaxone.com/injection-assistance/preparing-your-injection.html (last visited Mar. 7, 2016).
The National MS Society (USA) 2010. Available from: http://www.nationalmssociety.org/about-multiple-sclerosis/what-we-know-about-ms/treatments/index.aspx. Retrieved from: https://web.archive.org/web/20100204190658/http://www.nationalmssociety.org/about-multiple-sclerosis/what-we-know-about-ms/treatments/index.aspx.
Thrower (2007) Clinically isolated syndromes: predicting and delaying multiple sclerosis. Neurology 68(24 Suppl 4): S12-S15. Abstract.
Tintoré et al., (2006) Baseline MRI predicts future attacks and disability in clinically isolated syndromes. Neurology 67(6): 968-972.
Toutain and Bousquet-Melou (2004) Plasma terminal half-life. J Vet Pharmacol Ther 27(6): 427-439.
Tremlett et al., (2008) Relapses in multiple sclerosis are age- and time-dependent. J Neurol Neurosurg Psychiatry 79 (12): 1368-1374.
Tselis et al., (2007) Glatiramer acetate in the treatment of multiple sclerosis. Neuropsychiatr Dis Treat 3(2): 259-267.
Tysabri® Product Label (Oct. 2008).
U.S. Dep't Health & Human Servs., Common Terminology Criteria for Adverse Events (CTCAE) (Published: May 28, 2009 (v4.03: Jun. 14, 2010)). 196 pages.
Valeant Pharms. Int'l, Inc., Transcript of Jun. 17, 2014 Investor Presentation, http://1.usa.gov/21PTRZK.
Valenzuela et al., (2007) Clinical response to glatiramer acetate correlates with modulation of IFN-γ and IL-4 expression in multiple sclerosis. Mult Scler 13(6): 754-762.
Van Metre et al., (1996) Pain and dermal reaction caused by injected glycerin in immunotherapy solutions. J Allergy Clin Immunol 97(5): 1033-1039.
Varkony et al., (2009) The glatiramoid class of immunomodulator drugs. Expert Opin Pharmacother 10(4): 657-668.
Viglietta Vet al., (2004) Loss of functional suppression by CD4+ CD25+ regulatory T cells in patients with multiple sclerosis. J Exp Med 199(7): 971-979.
Virley (2005) Developing therapeutics for the treatment of multiple sclerosis. NeuroRx 2(4): 638-649.
Aharoni et al., (2008) Demyelination arrest and remyelination induced by glatiramer acetate treatment of experimental autoimmune encephalomyelitis. Proc Natl Acad Sci U S A 105(32): 11358-11363.
Anderson and Shive (1997) Biodegradation and biocompatibility of PLA and PLGA microspheres. Advanced Drug Delivery Reviews 64(Supplement): 72-82.
Bodmer et al., (1992) Factors influencing the release of peptides and proteins from biodegradable parenteral depot systems. Journal of Controlled Release 21(1-3): 129-137.
Bornstein et al., (1990), Clinical trials of Cop 1 in multiple sclerosis. In: Handbook of Multiple Sclerosis, ed. Cook S.D. Marcel Dekker, Inc., pp. 469-480.
Miller et al., (2007) Experimental autoimmune encephalomyelitis in the mouse. Current Protocols in Immunology 15.1.1-15.1.13.
Oraceska et al., "A comparison of dissolution properties from matrix tablets prepared from microcapsules and mixtures containing phenobarbitone and poly(DL-lactic acid)". In: Pharmaceutical Technology, Controlled Drug Release. Wells JI and Rubinstein MH (eds.). Taylor & Francis e-Library, 2005, pp. 141-151.
Ravivarapu et al., "Biodegradable Polymeric Delivery Systems". In: Design of Controlled Release Drug Delivery Systems. Li X and Jasti BR (eds.). McGraw-Hill Chemical Engineering, 2006, pp. 271-303.
Sabatos-Peyton et al., (2010) Antigen-specific immunotherapy of autoimmune and allergic diseases. Curr Opin Immunol 22(5): 609-615.
Sela et al., (1990) Suppressive activity of Cop-1 in EAE and its Relevance to Multiple Sclerosis. Bull Inst Pasteur 88: 303-314.
Teitelbaum et al., (1977) Suppression of experimental allergic encephalomyelitis in baboons by Cop 1. Israeli Med Sci. 13: 1038.
Teitelbaum et al., (1988) Specific inhibition of the T-cell response to myelin basic protein by the synthetic copolymer Cop 1. Proc Natl Acad Sci USA 85(24): 9724-97248.
"Design and development of sustained release or controlled release agents", chief edited by Yaodong Yan, Chinese medical science and technology press, First edition on May 2006; pp. 10-29. Translation of relevant portions.
Sustained-release Injectable Products, compiled by J. Senior, Chemistry Industry Press, First version in Sep. 2005, p. 88. Translation of relevant portions.
Lisak RP and Kira J-I 'Chapter 100, Multiple Sclerosis'. In: International Neurology a Clinical Approach. Edited by: Lisak et al., pp. 366-374, Wiley-Blackwell, 2009.
Lobel et al., (1996) Copolymer-1. Drugs of the Future 21(2): 131-134.
Lublin et al., (2003) Effect of relapses on development of residual deficit in multiple sclerosis. Neurology 61(11): 1528-1532.
Luzzio C & Keegan BM Multiple Sclerosis Medication, Medscape Reference (Nov. 24, 2014), retrieved on May 28, 2015. http://emedicine.medscape.com/article/1146199-medication#1.
Manso and Sokol (2006) Life cycle management of ageing pharmaceutical assets. Pharmaceutical Law Insight 3(7): 16-19.
Marketing Materials, PRA, Multiple Sclerosis: Transform Your Clinical Trial with PRA (2012) (on file with author) (Peroutka Dep. Ex. 4).
McBride (2002) Nonadherence to immunomodulation in multiple sclerosis. Int'l J MS Care 4: 85. Presented at the Second International Multiple Sclerosis Week. Multiple Sclerosis: A World View. Hyatt Regency Chicago, Illinois, USA; Jun. 5-9, 2002.

(56) References Cited

OTHER PUBLICATIONS

McDonald et al., (2001) Recommended diagnostic criteria for multiple sclerosis: Guidelines from the international panel on the diagnosis of multiple sclerosis. Annals of Neurology 50(1): 121-127.
McEwan et al., (2010) Best Practices in Skin Care for the Multiple Sclerosis Patient Receiving Injectable Therapies. Int J MS Care 12(4): 177-189.
McKeage (2015) Glatiramer Acetate 40 mg/mL in Relapsing-Remitting Multiple Sclerosis: A Review. CNS Drugs; Published online: Apr. 24, 2015. 8 pages.
Medical News Today; Multiple Sclerosis—Teva Provides Update on Forte Trial. Article Date: Jul. 8, 2008. Retrieved from: https://web.archive.org/web/20090103103610/http://www.medicalnewstoday.com/articles/114183.php; 3 pages.
Meibohm and Derendorf (1997) Basic concepts of pharmacokinetic/pharmacodynamic (PK/PD) modelling. Int J Clin Pharmacol Ther 35(10): 401-413.
Meiner Z et al., (1997) Copolymer 1 in relapsing-remitting multiple sclerosis: a multi-centre trial. In: Frontiers in Multiple Sclerosis: Clinical Research and Therapy. Edited by Abramsky O and Ovadia Hpp. 213-221.
Mendes and Sá (2011) Classical immunomodulatory therapy in multiple sclerosis: how it acts, how it works. Arq Neuropsiquiatr 69(3): 536-543.
Menge et al., (2008) Disease-modifying agents for multiple sclerosis: recent advances and future prospects. Drugs 68(17): 2445-2468.
Miller (2004) The importance of early diagnosis of multiple sclerosis. J Manag Care Pharm 10(3 Suppl B): S4-S11.
Miller et al., (1998) Treatment of multiple sclerosis with copolymer-1 (Copaxone®): implicating mechanisms of Th1 to Th2/Th3 immune-deviation. J Neuroimmunol 92(1-2): 113-121.
Miller et al., (2005) Clinically isolated syndromes suggestive of multiple sclerosis, part I: natural history, pathogenesis, diagnosis, and prognosis. Lancet Neurol 4(5): 281-288. Abstract.
Miller et al., (2005) Clinically isolated syndromes suggestive of multiple sclerosis, part 2: non-conventional MRI, recovery processes, and management. Lancet Neurol 4(6): 341-348. Abstract.
Minneboo et al., (2008) Predicting short-term disability progression in early multiple sclerosis: added value of MRI parameters. J Neurol Neurosurg Psychiatry 79(8): 917-923.
MomentumMagazineOnline.com; 10 Disease-Modifying Treatments, Nov. 2013, available at http://bit.ly/1eVa0jT.
Monro (1993) The paradoxical lack of interspecies correlation between plasma concentrations and chemical carcinogenicity. Regul Toxicol Pharmacol 18(1): 115-135.
Neuhaus et al., (2000) Multiple sclerosis: comparison of copolymer-1-reactive T cell lines from treated and untreated subjects reveals cytokine shift from T helper 1 to T helper 2 cells. Proc Natl Acad Sci U S A 97(13): 7452-7457.
Neuhaus et al., (2001) Mechanisms of action of glatiramer acetate in multiple sclerosis. Neurology 56(6): 702-708.
Neuhaus et al., (2003) Immunomodulation in multiple sclerosis: from immunosuppression to neuroprotection. Trends Pharmacol Sci 24(3): 131-138. Abstract.
Neuhaus et al., (2007) Pharmacokinetics and pharmacodynamics of the interferon-betas, glatiramer acetate, and mitoxantrone in multiple sclerosis. J Neurol Sci 259(1-2): 27-37.
Noseworthy et al., (2000) Multiple sclerosis. N Engl J Med 343(13): 938-952.
O'Connor et al., (2009) 250 microg or 500 microg interferon beta-1b versus 20 mg glatiramer acetate in relapsing-remitting multiple sclerosis: a prospective, randomised, multicentre study. Lancet Neurol 8(10): 889-897 with errata.
Oksenberg et al., (1992) A single amino-acid difference confers major pharmacological variation between human and rodent 5-HT1B receptors. Nature 360(6400): 161-163.
O'Neill (1997) Secondary endpoints cannot be validly analyzed if the primary endpoint does not demonstrate clear statistical significance. Controlled Clinical Trials 18(6): 550-556.
Opinion, *Endo Pharmaceuticals, Inc.* v. *Mylan Pharmaceuticals, Inc.*, No. 11-cv-00717, Document 226 (D. Del. Jan. 28, 2014) (Peroutka Dep. Ex. 6). 108 pages.
Orange Book: Approved Drug Products with Therapeutic Equivalence Evaluations. Retrieved from: http://www.accessdata.fda.gov/scripts/cder/ob/docs/patexclnew.cfm?Appl_No=020622&Product_No=003&table1=OB_Rx (accessed Feb. 5, 2015). 7 pages.
Orelli Brian; Momenta Slowed (Temporarily), The Motley Fool (Nov. 7, 2015), retrieved on Dec. 28, 2015. http://bit.ly/1YiNNmS.
Osborne (2009) Buzz around Campath proof-of-concept trial in MS. Nat Biotechnol 27(1): 6-8.
Paolillo et al., (2004) The relationship between inflammation and atrophy in clinically isolated syndromes suggestive of multiple sclerosis: a monthly MRI study after triple-dose gadolinium-DTPA. J Neurol 251(4): 432-439.
Pardo et al., (2007) Impact of an oral antihistamine on local injection site reactions with glatiramer acetate. Multiple Sclerosis 13: S134. Abstract P455.
Partidos et al., (2003) Immunity under the skin: potential application for topical delivery of vaccines. Vaccine 21(7-8): 776-780.
Paty (1994) The interferon-β1b clinical trial and its implications for other trials. Ann Neurol 36 Suppl: S113-S114.
Pelidou et al., (2008) Multiple sclerosis presented as clinically isolated syndrome: the need for early diagnosis and treatment. Ther Clin Risk Manag 4(3): 627-630.
Peroutka (1988) Antimigraine drug interactions with serotonin receptor subtypes in human brain. Ann Neurol 23(5): 500-504.
Pert and Snyder (1973) Properties of opiate-receptor binding in rat brain. Proc Natl Acad Sci U S A 70(8): 2243-2247.
Petty et al., (1994) The effect of systemically administered recombinant human nerve growth factor in healthy human subjects. Ann Neurol 36(2): 244-246.
Polman et al., (2005) Diagnostic criteria for multiple sclerosis: 2005 revisions to the "McDonald Criteria". Ann Neurol 58(6): 840-846.
Prescribing Information, EMD Serono, Rebif Prescribing Information (Sep. 2009).
Prescribing Information, Extavia (Interferon beta-1b) Kit for subcutaneous use Highlights of Prescribing Information (Aug. 2009) (on file with author).
Press Release, Biogen Idec, Inc., Avonex® (Interferon beta-1a) IM Injection (Oct. 2008) (on file with author).
Quintana et al., (2008) Systems biology approaches for the study of multiple sclerosis. J Cell Mol Med 12(4): 1087-1093.
Ramot et al., (2012) Comparative long-term preclinical safety evaluation of two glatiramoid compounds (Glatiramer Acetate, Copaxone(R), and TV-5010, protiramer) in rats and monkeys. Toxicol Pathol 40(1): 40-54.
Randall et al.,; Chapter 5: Approaches the the Analysis of Peptides. Peptide and Protein Drug Delivery, edited by Lee VHL. Marcel Dekker, Inc. New York, USA, 1991. pp. 203-246.
Rebif® Product Label (Jun. 2005).
Shenoy DB, D'Souza RJ, Udupa N, "Poly(DL-lactide-co-glycolide) microporous microsphere-based depot formulation of a peptide-like antineoplastic agent," Journal of Microencapsulation, 2002, 19(4): 523-535.*
Shenoy, D. B. et al., (2002) Poly(DL-lactide-co-glycolide) microporous microsphere-based depot formulation of a peptide-like antineoplastic agent. J Microencapsul 19(4):523-535.

* cited by examiner

DEPOT SYSTEMS COMPRISING GLATIRAMER OR PHARMACOLOGICALLY ACCEPTABLE SALT THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

*More than one reissue application has been filed for the reissue of U.S. Pat. No. 8,377,885. The reissue applications are application Ser. Nos. 17/213,352 (filed Mar. 26, 2021) and 17/894,447 (this application). This application is a continuation reissue of application Ser. No. 17/213,352, which is an application for reissue of U.S. Pat. No. 8,377,885.*

The present application is a *continuation reissue of application Ser. No. 17/213,352, which is an application for reissue of U.S. Pat. No. 8,377,885, which is a* Continuation-In-Part of U.S. patent application Ser. No. 13/258,808, filed on Sep. 22, 2011, which is a 35 U.S.C. § 371 National Phase Entry Application from PCT/IL2010/000679, filed Aug. 19, 2010, and designating the United States, which claims the benefit of U.S. Provisional Application No. 61/291,928, filed Jan. 4, 2010, the disclosure of which is incorporated herein in its entirety by reference.

*Therefore, this application is being filed as a continuation reissue application, meaning it is a continuation of reissue application Ser. No. 17/213,352, and is also a reissue of U.S. Pat. No. 8,377,885.*

FIELD OF THE INVENTION

The present invention relates to long acting dosage forms of glatiramer acetate and other pharmacologically acceptable salts of glatiramer. Particularly preferred are depot systems and other implantable systems for prolonged release of glatiramer acetate.

BACKGROUND OF THE INVENTION

Glatiramer Acetate

Copolymer-1, also known as glatiramer acetate and marketed under the tradename Copaxone®, comprises the acetate salts of polypeptides containing L-glutamic acid, L-alanine, L-tyrosine and L-lysine. The average molar fractions of the amino acids are 0.141, 0.427, 0.095 and 0.338, respectively, and the average molecular weight of copolymer-1 is between 4,700 and 11,000 daltons. Chemically, glatiramer acetate is designated L-glutamic acid polymer with L-alanine, L-lysine and L-tyrosine, acetate (salt). Its structural formula is:

$$(\text{Glu, Ala, Lys, Tyr})x\text{CH}_3\text{COOH}$$
$$(\text{C}_5\text{H}_9\text{NO}_4_\text{C}_3\text{H}_7\text{NO}_2_\text{C}_6\text{H}_{14}\text{N}_2\text{O}_2_\text{C}_9\text{H}_{11}\text{NO}_3)x\text{C}_2\text{H}_4\text{O}_2 \text{ [CAS—147245-92-9]},$$

approx. ratio $Glu_{14}Ala_{43}Tyr_{10}Lyz_{34}x(CH_3COOH)_{20}$. Copaxone® is a clear, colorless to slightly yellow, sterile, nonpyrogenic solution for subcutaneous injection. Each milliliter contains 20 mg of glatiramer acetate and 40 mg of mannitol. The pH range of the solution is approximately 5.5 to 7.0.

Mechanism of Action

Glatiramer acetate is a random polymer (average molecular mass 6.4 kD) composed of four amino acids that are found in myelin basic protein. The mechanism of action for glatiramer acetate is unknown, although some important immunological properties of this copolymer have emerged. Administration of copolymer-1 shifts the population of T cells from pro-inflammatory Th1 cells to regulatory Th2 cells that suppress the inflammatory response (FDA Copaxone® label). Given its resemblance to myelin basic protein, copolymer-1 may also act as a decoy, diverting an autoimmune response against myelin. The integrity of the blood-brain barrier, however, is not appreciably affected by copolymer-1, at least not in the early stages of treatment.

Copolymer-1 is a non-autoantigen which has been demonstrated to suppress experimental allergic encephalomyelitis (EAE) induced by various encephalitogens including mouse spinal cord homogenate (MSCH) which includes all myelin antigens, such as myelin basic protein (MBP) (Sela M et al., Bull Inst Pasteur (1990) 88 303-314), proteolipid protein (PLP) (Teitelbaum D et al., J Neuroimmunol (1996) 64 209-217) and myelin oligodendrocyte glycoprotein (MOG) (Ben-Nun A et al., J Neurol (1996) 243 (Suppl 1) S14-S22) in a variety of species. EAE is an accepted model for multiple sclerosis.

Copolymer-1 has been demonstrated to be active when injected subcutaneously, intraperitoneally, intravenously or intramuscularly (Teitelbaum D et al., Eur J Immunol (1971) 1 242-248; Teitelbaum D et al., Eur J Immunol (1973) 3 273-279). In phase III clinical trials, daily subcutaneous injections of copolymer-1 were found to slow the progression of disability and reduce the relapse rate in exacerbating-remitting multiple sclerosis (Johnson K P, Neurology (1995) 1 65-70; www.copaxone.com). Copolymer-1 therapy is presently limited to daily subcutaneous administration. Treatment with copolymer-1 by ingestion or inhalation is disclosed in U.S. Pat. No. 6,214,791, but these routes of administration have not been shown to attain clinical efficacy in human patients.

Efficacy

Evidence supporting the effectiveness of glatiramer acetate in decreasing the frequency of relapses in patients with Relapsing-Remitting Multiple Sclerosis (RR MS) derives from two placebo-controlled trials, both of which used a glatiramer acetate dose of 20 mg/day. No other dose or dosing regimen has been studied in placebo-controlled trials of RR MS (www.copaxone.com). A comparative trial of the approved 20 mg dose and the 40 mg dose showed no significant difference in efficacy between these doses (The 9006 trial; Cohen J A et al., Neurology (2007) 68 939-944). Various clinical trials in glatiramer acetate are on-going. These include studies with a higher dose of glatiramer acetate (40 mg—the FORTE study); studies in Clinically Isolated Syndrome patients (the PreCISe study) as well as numerous combination and induction protocols, in which glatiramer acetate is given together with or following another active product.

Side Effects

Currently, all specifically approved treatments of multiple sclerosis involve self injection of the active substance. Frequently observed injection-site problems include irritation, hypersensitivity, inflammation, pain and even necrosis (in the case of interferon 1β treatment) and a low level of patient compliance.

Side effects generally include a lump at the injection site (injection site reaction), aches, fever, and chills. These side effects are generally mild in nature. Occasionally a reaction occurs minutes after injection in which there is flushing, shortness in breath, anxiety and rapid heartbeat. These side effects subside within thirty minutes. Over time, a visible dent at the injection site due to the local destruction of fat tissue, known as lipoatrophy, may develop. Therefore, an alternative method of administration is desirable.

More serious side effects have been reported for glatiramer acetate, according to the FDA's prescribing label, these include serious side effects to the body's cardiovascular system, digestive system (including liver), hemic and lymphatic system, musculoskeletal system, nervous system, respiratory system, special senses (in particular the eyes), urogenital system; also reported have been metabolic and nutritional disorders; however a link between glatiramer acetate and these adverse effects has not been definitively established (FDA Copaxone® label).

Depot Systems

The parenteral route by intravenous (IV), intramuscular (IM), or subcutaneous (SC) injection is the most common and effective form of delivery for small as well as large molecular weight drugs. However, pain, discomfort and inconvenience due to needle sticks makes this mode of drug delivery the least preferred by patients. Therefore, any drug delivery technology that can at a minimum reduce the total number of injections is preferred. Such reductions in frequency of drug dosing in practice may be achieved through the use of injectable depot formulations that are capable of releasing drugs in a slow but predictable manner and consequently improve compliance. For most drugs, depending on the dose, it may be possible to reduce the injection frequency from daily to once or twice monthly or even longer (6 months). In addition to improving patient comfort, less frequent injections of drugs in the form of depot formulations smoothes out the plasma concentration-time profile by eliminating the hills and valleys. Such smoothing out of plasma profiles has the potential to not only boost the therapeutic benefit in most cases, but also to reduce any unwanted events, such as immunogenicity etc. often associated with large molecular weight drugs.

Microparticles, implants and gels are the most common forms of biodegradable polymeric devices used in practice for prolonging the release of drugs in the body. Microparticles are suspended in an aqueous media right before injection and one can load as much as 40% solids in suspensions. Implant/rod formulations are delivered to SC/IM tissue with the aid of special needles in the dry state without the need for an aqueous media. This feature of rods/implants allows for higher masses of formulation, as well as drug content to be delivered. Further, in the rods/implants, the initial burst problems are minimized due to much smaller area in implants compared to the microparticles. Besides biodegradable systems, there are non-biodegradable implants and infusion pumps that can be worn outside the body. Non-biodegradable implants require a doctor's visit not only for implanting the device into the SC/IM tissue but also to remove them after the drug release period.

Injectable compositions containing microparticle preparations are particularly susceptible to problems. Microparticle suspensions may contain as much as 40% solids as compared with 0.5-5% solids in other types of injectable suspensions. Further, microparticles used in injectable depot products, range in size up to about 250 μm (average, 60-100 μm), as compared with a particle size of less than 5 μm recommended for IM or SC administration. The higher concentrations of solids, as well as the larger solid particle size require larger size of needle (around 18-21 gauge) for injection. Overall, despite the infrequent uses of larger and uncomfortable needles, patients still prefer less frequently administered dosage forms over everyday drug injections with a smaller needle.

Biodegradable polyesters of poly(lactic acid) (PLA) and copolymers of lactide and glycolide referred to as poly (lactide-co-glycolide) (PLGA) are the most common polymers used in biodegradable dosage forms. PLA is hydrophobic molecule and PLGA degrades faster than PLA because of the presence of more hydrophilic glycolide groups. These biocompatible polymers undergo random, non-enzymatic, hydrolytic cleavage of the ester linkages to form lactic acid and glycolic acid, which are normal metabolic compounds in the body. Resorbable sutures, clips and implants are the earliest applications of these polymers. Southern Research Institute developed the first synthetic, resorbable suture (Dexon®) in 1970. The first patent describing the use of PLGA polymers in a sustained release dosage form appeared in 1973 (U.S. Pat. No. 3,773,919).

Today, PLGA polymers are commercially available from multiple suppliers; Alkermes (Medisorb polymers), Absorbable Polymers International [formerly Birmingham Polymers (a Division of Durect)], Purac and Boehringer Ingelheim. Besides PLGA and PLA, natural cellulosic polymers such as starch, starch derivatives, dextran and non-PLGA synthetic polymers are also being explored as biodegradable polymers in such systems.

At present no long acting dosage forms of glatiramer acetate are available. This is a huge unmet medical need, as these formulations would be extremely beneficial to many patients, particularly to those with neurological symptoms or physical disabilities.

SUMMARY OF THE INVENTION

The present invention provides long acting parenteral pharmaceutical compositions comprising a therapeutically effective amount of a pharmaceutically acceptable salt of glatiramer, e.g., glatiramer acetate. In particular, the present invention provides a long acting pharmaceutical composition comprising a therapeutically effective amount of glatiramer salt in a depot form, suitable for parenteral administration at a medically acceptable location in a subject in need thereof. The present invention further provides a method of treating multiple sclerosis, comprising the parenteral administration or implantation of a composition comprising a therapeutically effective amount of a pharmaceutically acceptable salt of glatiramer, preferably glatiramer acetate.

Unexpectedly it has now been discovered that the long acting pharmaceutical compositions according to the principles of the present invention provide equal or superior therapeutic efficacy to the commercially available daily injectable dosage forms, with reduced incidence and/or severity of side effects at the local and/or systemic levels.

According to some embodiments, the glatiramer acetate comprises the acetate salt of L-alanine, L-glutamic acid, L-lysine, and L-tyrosine in the molar ratios of about 0.14 glutamic acid, about 0.43 alanine, about 0.10 tyrosine and about 0.33 lysine.

According to other embodiments, the glatiramer acetate or other pharmaceutically acceptable salt of glatiramer comprises about 15 to about 100 amino acids.

According to certain embodiments, the implantable depot is suitable for subcutaneous or intramuscular implantation.

According to alternative embodiments, the long acting parenteral pharmaceutical composition comprises a pharmaceutically acceptable biodegradable or non-biodegradable carrier for glatiramer salts such as glatiramer acetate.

According to some embodiments, the carrier is selected from PLGA, PLA, PGA, polycaprolactone, polyhydroxybutyrate, polyorthoesters, polyalkaneanhydrides, gelatin, collagen, oxidized cellulose, and polyphosphazene. Each possibility represents a separate embodiment of the invention.

According to particular embodiments, the long acting pharmaceutical compositions of the present invention are in the form of microparticles prepared by a water-in oil-in water double emulsification process. In currently preferred embodiments, the long acting pharmaceutical compositions of the present invention comprise an internal aqueous phase comprising a therapeutically effective amount of a pharmaceutically acceptable salt of glatiramer, a water immiscible polymeric phase comprising a carrier selected from a biodegradable and a non-biodegradable polymer, and an external aqueous phase. In other currently preferred embodiments, the water immiscible polymeric phase comprises a biodegradable polymer selected from PLA and PLGA. Each possibility represents a separate embodiment of the invention. In additional embodiments, the external aqueous phase comprises a surfactant selected from polyvinyl alcohol (PVA), polysorbate, polyethylene oxide-polypropylene oxide block copolymers and cellulose esters. Each possibility represents a separate embodiment of the invention.

The present invention encompasses the use of glatiramer acetate or any other pharmaceutically acceptable salt of glatiramer in depot form suitable for implantation into an individual in need thereof for treating multiple sclerosis.

The present invention further encompasses the use of the implantable depot of glatiramer acetate suitable for providing prolonged release or prolonged action of glatiramer in a subject.

Within the scope of the present invention is a pharmaceutically acceptable salt of glatiramer in depot form suitable for use in the treatment of multiple sclerosis or in providing prolonged release or prolonged action of glatiramer in a subject.

The invention also encompasses the combination of glatiramer acetate with at least one additional drug, preferably, an immunosuppressant, particularly fingolimod.

According to some embodiments, the long acting pharmaceutical composition is suitable for a dosing schedule from once weekly to once in every 6 months.

According to particular embodiments, the composition is suitable for dosing from once every 2 weeks to once monthly.

According to some embodiments, the long acting compositions comprise a dose between 20-750 mg of glatiramer acetate per injection.

Specific examples of the long acting compositions will include biodegradable or non-biodegradable microspheres, implants of any suitable geometric shape, implantable rods, implantable capsules, implantable rings, prolonged release gels and erodible matrices. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
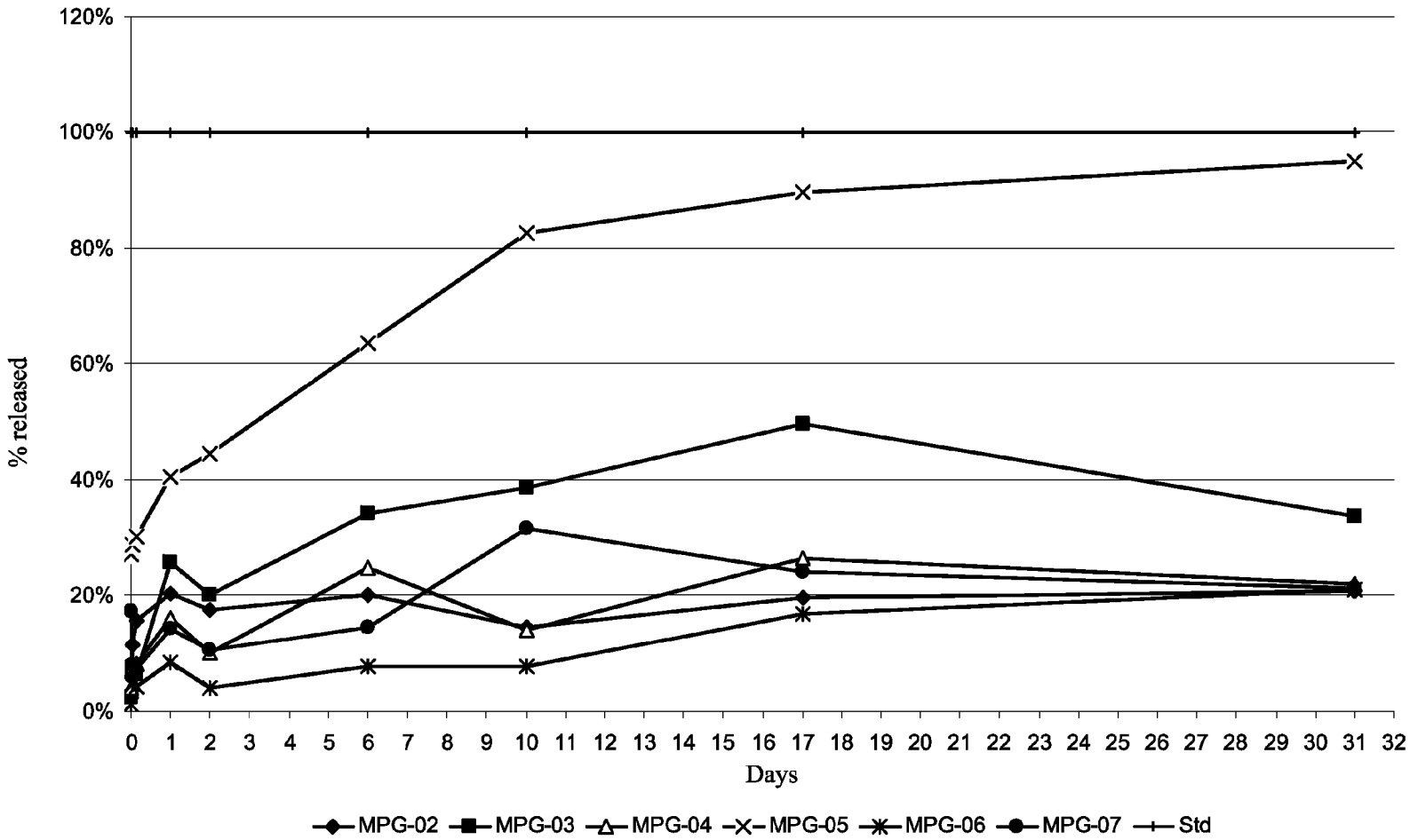
FIG. 1. Release of glatiramer acetate from PLGA microparticulate formulations MPG-02-07 in PBS at 37° C. Data represented are normalized to standard peptide solution stored in same conditions.

The present invention provides pharmaceutical preparations of pharmaceutically acceptable salts of glatiramer, preferably glatiramer acetate, for sustained release by parenteral administration, which afford equal or superior therapeutic efficacy to the daily injections and thus result in improved patient compliance. In addition to providing the same therapeutic efficacy, the long acting injections or implants reduce the glatiramer side effects (local and/or systemic), resulting from frequent injections.

According to a first aspect, the present invention provides a parenteral pharmaceutical composition comprising a therapeutically effective amount of glatiramer acetate or any other pharmaceutically acceptable salt of glatiramer. The term "parenteral" as used herein refers to routs selected from subcutaneous (SC), intravenous (IV), intramuscular (IM), intradermal (ID), intraperitoneal (IP) and the like. Each possibility represents a separate embodiment of the invention. The term "therapeutically effective amount" as used herein is intended to qualify the amount of copolymer that will achieve the goal of alleviation of the symptoms of multiple sclerosis. Suitable doses include, but are not limited to, 20-750 mg for each dosage form. However, it is understood that the amount of the copolymer administered will be determined by a physician, according to various parameters including the chosen route of administration, the age, weight, and the severity of the patient's symptoms. According to various embodiments of the present invention, the therapeutically effective amount of the at least one copolymer ranges from about 1 mg to about 500 mg/day. Alternatively, such therapeutically effective amounts of the at least one copolymer are from about 20 mg to about 100 mg/day.

In another aspect, the present invention provides a long acting pharmaceutical composition comprising a therapeutically effective amount of glatiramer acetate or any other pharmaceutically acceptable salt of glatiramer in a depot form suitable for administration at a medically acceptable location in a subject in need thereof The term "long acting" as used herein refers to a composition which provides prolonged, sustained or extended release of the glatiramer salt to the general systemic circulation of a subject or to local sites of action in a subject. This term may further refer to a composition which provides prolonged, sustained or extended duration of action (pharmacokinetics) of the glatiramer salt in a subject. In particular, the long acting pharmaceutical compositions of the present invention provide a dosing regimen which ranges from once weekly to once every 6 months. According to currently more preferable embodiments, the dosing regimen ranges from once a week, twice monthly (approximately once in every 2 weeks) to once monthly. Depending on the duration of action required, each depot or implantable device of the present invention will typically contain between about 20 and 750 mg of the active ingredient, designed to be released over a period ranging from a couple of weeks to a number of months.

In some embodiments, the depot formulations of the present invention include, but are not limited to, suspensions of glatiramer or a pharmaceutically acceptable salt thereof in water, oil or wax phase; poorly soluble polyelectrolyte complexes of glatiramer or a pharmaceutically acceptable salt thereof; "in-situ" gel-forming matrices based on the combination of water-miscible solvent with glatiramer or a pharmaceutically acceptable salt thereof; and biodegradable polymeric microparticles with incorporated glatiramer or a pharmaceutically acceptable salt thereof. Each possibility represents a separate embodiment of the invention. In particular, the compositions of the present invention are in the form of injectable microparticles wherein the glatiramer or pharmaceutically acceptable salt thereof is entrapped in a biodegradable or non-biodegradable carrier. The microparticulate compositions of the present invention may comprise a water-in oil-in water double emulsion. Within the scope of the present invention is a microparticulate composition comprising an internal aqueous phase comprising glatiramer or any pharmaceutically acceptable salt thereof, an oil phase or water-immiscible phase comprising a biodegradable or non-biodegradable polymer and an external aqueous phase. The external aqueous phase may further comprise a surfactant, preferably polyvinyl alcohol (PVA), polysorbate, polyethylene oxide-polypropylene oxide block copolymers or cellulose esters. The terms "oil phase" and "water-immiscible phase" may be used interchangeably herein.

The present invention further provides a method of treating multiple sclerosis by parenteral administration of a long acting pharmaceutical composition comprising a therapeutically effective amount of glatiramer acetate or any other pharmaceutically acceptable salt of glatiramer to a subject in need thereof. Within the scope of the present invention is a method of treating multiple sclerosis, by administration into an individual in need thereof, glatiramer acetate or any other pharmaceutically acceptable salt of glatiramer in a depot form. The term "treating" as used herein refers to suppression or alleviation of symptoms after the onset of multiple sclerosis. Common symptoms after the onset of multiple sclerosis include, but are not limited to, reduced or loss of vision, stumbling and uneven gait, slurred speech, as well as urinary frequency and incontinence. In addition, multiple sclerosis can cause mood changes and depression, muscle spasms and severe paralysis. The "subject" to which the drug is administered is a mammal, preferably, but not limited to, a human. The term "multiple sclerosis" as used herein refers to an auto-immune disease of the central nervous system which is accompanied by one or more of the symptoms described hereinabove.

The term "glatiramer acetate" as used herein refers to a compound formerly known as Copolymer 1 that is sold under the trade name Copaxone® and consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate in Copaxone® is 4,700-11,000 daltons (FDA Copaxone® label) and the number of amino acid ranges between about 15 to about 100 amino acids. The term also refers to chemical derivatives and analogues of the compound. Typically the compound is prepared and characterized as specified in any of U.S. Pat. Nos. 5,981,589; 6,054,430; 6,342,476; 6,362,161; 6,620,847; and 6,939,539, the contents of each of these references are hereby incorporated in their entirety.

In some embodiments, the composition may comprise any other pharmaceutically acceptable salt of glatiramer including, but not limited to, sulfate, pyrosulfate, bisulfate, sulfite, bisulfate, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, tocopheryl succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-2-sulfonate, p-toluenesulfonate, mandelate and the like salts. Each possibility represents a separate embodiment of the invention.

The copolymers can be made by any procedure available to one of skill in the art. For example, the copolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example, dicyclohexylcarbodiimide, can be used to facilitate the formation of the peptide bond.

Blocking groups can be used to protect functional groups, such as the side chain moieties and some of the amino or carboxyl groups against undesired side reactions. The process disclosed in U.S. Pat. No. 3,849,550, the contents of which are hereby incorporated by reference in its entirety, can be used for preparing the copolymers of the invention. For example, the N-carboxyanhydrides of tyrosine, alanine, γ-benzyl glutamate and N, ϵ-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by one molar piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine. U.S. Pat. Nos. 6,620,847; 6,362,161; 6,342,476; 6,054,430; 6,048,898 and 5,981,589, the content of which are hereby incorporated by reference in their entirety, disclose improved methods for preparing glatiramer acetate (Cop-1). For purposes of this application, the terms "ambient temperature" and "room temperature" typically means a temperature ranging from about 20° C. to about 26° C.

The molecular weight of the copolymers can be adjusted during polypeptide synthesis or after the polymers have been made. To adjust the molecular weight during polypeptide synthesis, the synthetic conditions or the amounts of amino acids are adjusted so that synthesis stops when the polypeptide reaches the approximate desired length. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the copolymers with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by the test reaction. The trifluoroacetyl-polypeptide with the desired molecular weight profile is then further treated with an aqueous piperidine solution to form a deprotected polypeptide having the desired molecular weight.

In a preferred embodiment, a test sample of protected polypeptide from a given batch is reacted with hydrobromic acid for about 10-50 hours at a temperature of about 20-28° C. The best conditions for that batch are determined by running several test reactions. For example, in one embodiment, the protected polypeptide is reacted with hydrobromic acid for about 17 hours at a temperature of about 26° C.

In certain embodiments, the dosage forms include, but are not limited to, biodegradable injectable depot systems such as, PLGA based injectable depot systems; non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as Poly(e-caprolactone) i.e. PCL (Lactel® from Durect); polyanhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly(p-{carboxyphenoxy}methane), CPM; poly(p-{carboxyphenoxy}propane), CPP; poly(p-{carboxyphenoxy}hexane)s CPH; polyamines, polyurethanes, polyesteramides, polyorthoesters {CHDM: cis/trans-cyclohexyl dimethanol, HD:1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) tri-block copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof.

In some embodiments, the compositions of the present invention comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphosphazene and the like. Each possibility represents a separate embodiment.

Currently preferred biodegradable polymer is a lactic acid-based polymer, more preferably polylactide, or poly (D,L-lactide-co-glycolide) i.e. PLGA. Preferably, the biodegradable polymer is present in an amount between about 10% to about 98% w/w of the composition. The lactic acid-based polymer has a monomer ratio of lactic acid to glycolic acid in the range of 100:0 to about 0:100, preferably 100:0 to about 10:90 and has an average molecular weight of from about 1,000 to 200,000 daltons. However, it is understood that the amount of biodegradable polymer is determined by parameters such as the duration of use and the like.

The compositions of the present invention may further comprise one or more pharmaceutically acceptable excipient(s) selected from, but not limited to, co-surfactants, solvents/co-solvents, water immiscible solvents, water, water miscible solvents, oily components, hydrophilic solvents, emulsifiers, preservatives, antioxidants, anti-foaming agents, stabilizers, buffering agents, pH adjusting agents, osmotic agents, channel forming agents, osmotic adjustment agents, or any other excipient known in the art. Suitable co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Each possibility represents a separate embodiment of the invention. Suitable solvents/co-solvents include, but not limited to, alcohols, triacetin, dimethyl isosorbide, glycofurol, propylene carbonate, water, dimethyl acetamide, and the like or mixtures thereof. Each possibility represents a separate embodiment of the invention. Suitable anti-foaming agents include, but are not limited to, silicon emulsions or sorbitan sesquioleate. Suitable stabilizers to prevent or reduce the deterioration of the components in the compositions of the present invention include, but are not limited to, antioxidants such as glycine, α-tocopherol or ascorbate, BHA, BHT, and the like or mixtures thereof. Each possibility represents a separate embodiment of the invention. Suitable tonicity modifiers include, but are not limited to, mannitol, sodium chloride, and glucose. Each possibility represents a separate embodiment of the invention. Suitable buffering agents include, but are not limited to, acetates, phosphates, and citrates with suitable cations. Each possibility represents a separate embodiment of the invention.

The compositions of the present invention can be prepared by any manner known in the art. Currently preferred is the incorporation of the glatiramer or salt thereof copolymer into a colloidal delivery system, e.g., biodegradable microparticles, thus allowing release retardation by diffusion through polymeric walls of the particle and by polymer degradation in water media or biological fluids in the body. The compositions of the present invention can be prepared in the form of injectable microparticles by a process known as the "double emulsification". Briefly, the concentrated solution of the water-soluble copolymer is dispersed in a solution of the biodegradable or non-biodegradable polymer in water-immiscible volatile organic solvent (e.g. methylene chloride, chloroform and the like). The thus obtained "water-in-oil" (w/o) emulsion is then dispersed in a continuous external water phase containing surfactant (e.g. polyvinyl alcohol—PVA, polysorbates, polyethylene oxide-polypropylene oxide block copolymers, cellulose esters and the like) to form "water-in oil-in water (w/o/w) double emulsion" droplets. After evaporation of the organic solvent, the microparticles solidify and are collected by filtration or centrifugation. The collected microparticles (MPs) are washed with purified water to eliminate most of the surfactant and non-bonded peptide and centrifugated again. The washed MPs are collected and lyophilized without additives or with the addition of cryoprotectant (mannitol) to facilitate their subsequent reconstitution.

The particle size of the "water-in oil-in water (w/o/w) double emulsion" can be determined by various parameters including, but not limited to, the amount of applied force at this step, the speed of mixing, surfactant type and concentration, etc. Suitable particle sizes range from about 1 to 100 μm.

The depot systems of the present invention encompass any forms known to a person of skill in the art. Suitable forms include, but are not limited to, biodegradable or non biodegradable microspheres, implantable rods, implantable capsules, and implantable rings. Each possibility represents a separate embodiment of the invention. Further contemplated are prolonged release gel depot and erodible matrices. Each possibility represents a separate embodiment of the invention. Suitable implantable systems are described for example in US 2008/0063687, the content of which is hereby incorporated in its entirety. Implantable rods can be prepared as is known in the art using suitable micro-extruders.

According to the principles of the present invention, the long acting pharmaceutical compositions of the present invention provide equal or superior therapeutic efficacy to the commercially available daily injectable dosage forms, with reduced incidence of side effects and with reduced severity of side effects at the local and/or systemic level. In some embodiments, the compositions of the present invention provide prolonged release or prolonged action of glatiramer in a subject as compared to a substantially similar dose of an immediate release formulation of glatiramer acetate.

Encompassed by the present invention is a combination therapy of glatiramer acetate or any other pharmaceutically acceptable salt of glatiramer with at least one other active agent. Active agents within the scope of the present invention include, but are not limited to interferons, e.g. pegylated or non-pegylated α-interferons, or β-interferons, e.g. interferon β-1a or interferon β-1b, or τ-interferons; immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH; adenosine deaminase inhibitors, e.g. cladribine; IV immunoglobulin G (e.g. as disclosed in Neurology, 1998, May 50(5):1273-81) monoclonal antibodies to various T-cell surface markers, e.g. natalizumab (ANTEGREN®) or alemtuzumab; TH2 promoting cytokines, e.g. IL-4, IL-10, or compounds which inhibit expression of TH1 promoting cytokines, e.g. phosphodiesterase inhibitors, e.g. pentoxifylline; antispasticity agents including baclofen, diazepam, piracetam, dantrolene, lamotrigine, rifluzole, tizanidine, clonidine, beta blockers, cyproheptadine, orphenadrine or cannabinoids; AMPA glutamate receptor antagonists, e.g. 2,3-dihydroxy-6-nitro-7-sulfamoylbenzo(f)quinoxaline, [1,2,3,4,-tetrahydro-7-morpholin-yl-2,3-dioxo-6-(trifluoromethyl)quinoxalin-i-yl]methylphosphonate, 1-(4-aminophenyl)-4-methyl-7,8-methylene-dioxy-5H-2,3-benzodiazepine, or (−)1-(4-aminophenyl)-4-methyl-7,8-methylenedioxy-4,5-dihydro-3-methylcarbamoyl-2,3-benzodiazepine; inhibitors of VCAM-1 expression or antagonists of its ligand, e.g. antagonists of the α4β1 integrin VLA-4 and/or α-4-β-7 integrins, e.g. natalizumab (ANTEGREN®); anti-macrophage migration inhibitory factor (Anti-MIF); xii) Cathepsin S inhibitors; xiii) mTor inhibitors. Each possibility represents a separate embodiment of the invention. Currently preferred one other active agent is FTY720 (2-amino-2-[2-(4-octylphenyl)ethyl]propane-1,3-diol; fingolimod) belonging to the class of immunosuppressants.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

General Preparation Methods

PLGA Based Injectable Depot Particles

Microparticles were prepared by solvent extraction/evaporation method (single emulsion). A solution of 50:50, dichloromethane/ethanol containing 250 mg PLGA and 200 mg glatiramer acetate was slowly poured into an aqueous solution (200 ml) containing 2% PVA and emulsified using a mechanical stirrer (300 rpm) at 25° C. The organic solvent was evaporated under stirring (100 rpm) for 2 h. The thus formed microparticles were collected by centrifugation and washed with distilled water to remove excessive emulsifier. The final suspension was then freeze-dried to obtain a fine powder.

Polycaprolactone Based Injectable Depot Particles

Microparticles were prepared by solvent extraction/evaporation method (single emulsion). A solution of 70:30, dichloromethane/acetone containing 500 mg polycaprolactone and 200 mg glatiramer acetate was slowly poured into an aqueous solution (200 ml) containing 2% PVA, 1% Tween 80 and emulsified using mechanical stirrer (500 rpm) at 25° C. The organic solvent was evaporated under stirring (300 rpm) for 4 h. The formed microparticles were collected by centrifugation and washed with distilled water to remove excessive emulsifiers. The final suspension was then freeze dried to obtain a fine powder.

PLGA Based Implant-Rods

PLGA based biodegradable rod shaped implants, 20 mm in length and 2 mm in diameter, were prepared by solvent extraction/evaporation method. A solution of 50:50, dichloromethane/ethanol containing 250 mg PLGA and 200 mg glatiramer acetate was slowly poured into special rod shaped mold. The organic solvent was evaporated in vacuum oven during 12 hrs at room temperature. Alternatively the rod shaped implant was prepared by extrusion of the mixture of 250 mg PLGA and 200 mg of glatiramer at 85-90° C., using a screw type extruder (Microtruder Rancastle RCP-0250 or similar), with die diameter 0.8 or 1.0 mm.

Example 2

Analytical Method—Assay of Glatiramer Acetate

Equipment

Spectrophotometer

Analytical balance, capable of accurately weighing to 0.01 mg

Materials and Reagents

Glatiramer acetate 83% as a reference standard 2,4,6-trinitrobenzenesulfonic acid (TNBS, picrylsulfonic acid, 170.5 mM) 5% in MeOH 0.1 M borate buffer pH 9.3 (sodium tetraborate decahydrate MW 381.37)

water, purified volumetric pipettes for 0.5, 1.0, 2.0 and 7.0 mL miscellaneous glassware.

Preparations

Preparation of Glatiramer Stock Solution 400 ng/mL 4.8 mg of glatiramer acetate (potency 83% as base for reference standard) were weighed into a 10 ml volumetric flask. Approximately 7 ml of 0.1M borate buffer were added to afford dissolution of the glatiramer acetate in ultrasonic bath. The solution was further diluted with 0.1M borate buffer to obtain glatiramer stock solution 400 μg/ml (as base).

Preparation of 0.25% TNBS Working Solution

Prior to the use, 5% stock solution of TNBS was diluted with water (20 times; e.g. 50 μl and 950 μl of water) to obtain 0.25% TNBS working solution.

Calibration Curve Standards Preparation

Eight glatiramer calibration standard solutions (cSTD; 4 ml each) were prepared according to Table 1.

TABLE 1

Standard solutions of glatiramer acetate

| cSTD # | Concentration of glatiramer μg/ml (as base) | Volume of glatiramer stock solution (ml) | Volume of glatiramer Std 3 (ml) | Volume of 0.1M Borate buffer (ml) |
|---|---|---|---|---|
| Std 0 | 0 | | — | 4 |
| Std 1 | 2 | | 0.4 | 3.6 |
| Std 2 | 10 | | 2 | 2 |
| Std 3 | 20 | 0.2 | | 3.8 |
| Std 4 | 50 | 0.5 | | 3.5 |
| Std 5 | 100 | 1 | | 3 |
| Std 6 | 200 | 2 | | 2 |
| Std 7 | 400 | 4 | | — |

Optical Density Measurement 1.0 ml of each glatiramer calibration standard solutions, samples (in duplicate) and reagent blank (0.1M borate buffer) were transferred into 1.5 ml polypropylene centrifuge tube, to which 50 μl of 0.25% TNBS working solution was added. The solution was thoroughly mixed and kept at room temperature for 30 minutes. The optical densities of each of the obtained solutions were read at 420 nm and 700 nm and the difference of these densities were calculated to avoid error due to light dispersion in colloidal systems. A calibration curve for the selected range of concentrations was calculated.

Acceptance Criteria

The difference between results for duplicate sample preparations was NMT 5%, calculated by following equation:

$$D = \frac{(Rsp11 - Rsp12) \times 2}{Rsp11 + Rsp12} \times 100,$$

in which Rsp11 is the result obtained for sample 1 and Rsp12 is the result obtained for sample 2.

Example 3

Preparation of PLGA Microparticles Loaded with Glatiramer Acetate

External (continuous) water phase: 30 ml of 0.75% NaCl solution in purified water, further containing 0.5% partially hydrolyzed (87-89%) polyvinyl alcohol (PVA) as a surfactant, 0.2% polysorbate-80 (Tween-80) for MPG-10 and 2% PVA for blank MP preparation.

Internal water phase (for peptide solution): 150-200 μl of purified water per 25-30 mg of glatiramer acetate. The glatiramer acetate was dissolved in water using an ultrasonic bath.

Organic polymeric solution (oil phase): 165-300 mg of PLGA in 2-5 mL of methylene chloride. Optionally, a counter-ion was further dissolved or dispersed in the organic phase.

Preparation Proceedings

Water in oil (w/o) emulsion preparation: Internal water phase, containing dissolved glatiramer acetate, was mixed directly in the test tube with the oil phase containing PLGA solution in $CH_2Cl_2$. The mixture was thoroughly shaken and treated with ultrasonic indenter (titanium tip, max. power 120 watt, working power 10-15%, 3-5 cycles of 5 seconds). Cooling was optionally applied using ice or ice water to avoid boiling of methylene chloride.

Double emulsion (w/o/w) preparation: The thus obtained w/o emulsion of the glatiramer acetate solution in polymeric PLGA organic solution, was further treated with high shear mixer (small mixer, VDI-12, shaft diameter 10 mm, and bigger mixer, OMNI-1100, shaft diameter 18 mm) at various speeds for 30-120 seconds.

Solvent elimination: an open beaker with the thus formed double emulsion was placed on the magnetic plate stirrer and stirred for 3-4 hours at room temperature in a fume hood until all methylene chloride evaporated and the microparticles had solidified.

Centrifugation of microparticles: The suspension of solidified microparticles was centrifugated at 2000-5000 g for 10 minutes, the supernatant was transferred into a separate vessel and analyzed for glatiramer acetate content to estimate the peptide incorporation and binding.

Washing of microparticles: the sedimented microparticles from the above described procedure were suspended in 10 ml of purified water using vortex and an ultrasonic bath and shaken or sonicated for 2-3 minutes. The suspension of the microparticles was centrifuged again at 2000-5000 g for 10 minutes, the supernatant was transferred to a separate vessel and analyzed for glatiramer acetate content.

Lyophilization: The washed precipitate of microparticles was re-suspended in 3-5 ml of purified water or 5% mannitol, transferred to 10 ml pre-weighed glass vials, frozen using lyophilizer plate set at −37-43° C. and lyophilized (main drying for 16-48 hours at −20° C. and vacuum 0.05 bar, final drying for +12-16 hours at +20° C. and 0.025 bar). Vials after lyophilizing were weighed, closed with bromobutyl rubber stoppers and stored at refrigerator storage conditions until use.

Particle size estimation: particle size of the microparticles was evaluated using light field and phase contrast microscopy (Leutz Orthoplan™, Germany) with objectives 40× and 10× and stage micrometer with range of 1-1000 μm.

All microparticle formulations were prepared using water phase containing 0.75% sodium chloride to increase the external osmotic pressure and to improve the incorporation of the water-soluble charged drug. Blank (empty) microparticles (first experiment) were obtained with 2% PVA as a surfactant, whereas for the preparation of all peptide loaded formulations 0.5% PVA was used.

Compositions and parameters of the preparation process are presented in Tables 2-5.

TABLE 2

PLGA microparticles for sustained release of glatiramer acetate (GA) (formulations 1-4)

| | MP Blank | MPG-01 | MPG-02 | MPG-03 | MPG-04 |
|---|---|---|---|---|---|
| Internal water phase | | | | | |
| GA, mg | | 17 | 60.25 | 30 | 18.7 |
| GA dry base, mg | 0 | 14.11 | 50.0 | 24.9 | 15.5 |
| Water for GA, μl | | 100 | 400 | 200 | 100 + 50 μl of 2% PVA |
| Polymer in the oil phase | | | | | |
| PLGA RG 502H, mg | 215 | 270 | | | 165 |
| PLGA RG 502, mg | | | 500 | 220 | |
| Oil phase | | | | | |
| Tocopheryl succinate | | 100 | 120 | 50 | 65 |
| Methylene chloride | 2 ml (2.3 g) | 4.5 g | 9 g | 3.2 g | 3 g |
| External water phase | | | | | |
| PVA (2% or 0.5%) | 23 ml 2% | 65 ml 0.5% | 60 ml 0.5% | 30 ml 0.5% | 30 ml 0.5% |
| NaCl | 0 | 0.5 g | 0.5 g | 0.25 g | 0.25 g |
| Preparation process description (processor, speed set, evaporation duration) | IKA VDI-12 #5 30 sec, evap. overnight RT magnetic stirrer | IKA VDI-12 #5 2 min, evap. overnight RT magnetic stirrer | IKA VDI-12 #5 2 min, evap. overnight RT magnetic stirrer | IKA VDI-12 #5 2 min, evap. 4 hr RT magnetic stirrer | IKA VDI-12 #5 2 min, evap. 4 hr RT magnetic stirrer |
| Microparticles description | spherical MP 10-50 μm smooth surface | spherical MP 5-20 μm porous surface | aggregate MP 10-30 μm porous surface | spherical MP 10-15 μm slightly porous surface | spherical MP 10-15 μm slightly porous surface |
| Binding (association with MPs) | | 86% | 34% | 61% | 70% |

VWR VDI-12 high shear mixer from IKA Germany with small diameter of the stator (shaft 12 mm) and speed range 8-30,000 rpm was set in position #5 (approx. 24,000 rpm). Short treatment (30 sec) of approx. 10% PLGA solution in methylene chloride in 2% PVA phase was used to prepare blank MP sample, which resulted in smooth spherical microparticles with relatively wide size distribution (10-50 μm). Due to foaming, further process was carried out at lower concentration of surfactant. Homogenization time was also extended (1 or 2 minutes treatment) to obtain a more narrow size distribution.

Due to the presence of internal water phase in the double emulsion, all the microparticles prepared with the glatiramer peptide had visible inclusions and porosity signs either on the MP surface or inside the particle, when observed under optical microscope.

TABLE 3

PLGA microparticles for sustained release of glatiramer acetate (GA) (formulations 5-7)

| | MPG-05 | MPG-06 | MPG-07 |
|---|---|---|---|
| Internal water phase | | | |
| GA, mg | 30.8 | 20 | 20 |
| GA dry base, mg | 25.6 | 16.6 | 16.6 |
| Water for GA, μl | 100 + 50 PVA 2% | 166 | 175 |
| Polymer in the oil phase | | | |
| PLGA RG 502H, mg | 165 | | |
| PLGA RG 502, mg | | 200 | 250 |
| Oil phase | | | |
| Dicetylphosphate | | 75 | |
| Dimyristoylphosphatidyl glycerol sodium (DMPG Na) | | | 60 |
| Methylene chloride | 2.7 g | 2.5 g | 3.25 g |

TABLE 3-continued

PLGA microparticles for sustained release of glatiramer acetate (GA) (formulations 5-7)

| | MPG-05 | MPG-06 | MPG-07 |
|---|---|---|---|
| External water phase | | | |
| PVA (0.5%) | 30 ml | 30 ml | 30 ml |
| NaCl | 0.25 g | 0.25 g | 0.25 g |
| Observations and comments | | Flakes formed from DCP and GA | DMPG Na is poorly soluble in $CH_2Cl_2$ |
| Preparation process description (processor, speed set, evaporation duration) | IKA VDI-12 #5 2 min, evaporation 4 hr RT magetic stirrer | IKA VDI-12 #5 2 min, evaporation 4 hr RT magnetic stirrer | IKA VDI-12 #5 2 min, evaporation 4 hr RT magnetic stirrer |
| Microparticles description | spherical MP 10-15 μm slightly porous surface | irregular particles | spherical MP 5-15 μm |
| Binding (association with MPs) | 81% | 76% | 84% |

The formed glatiramer acetate loaded microparticles were centrifugated; the pellet was re-suspended in purified water, washed and repeatedly centrifuged. Supernatant and in some cases washing water were analyzed for glatiramer acetate content. The centrifugated precipitate was re-suspended in purified water or 5% mannitol solution and lyophilized.

TABLE 4

PLGA microparticles for sustained release of glatiramer acetate (GA) (formulations 05R, 08-011 and tocopheryl succinate salt of glatiramer)

| | MPG-08 | MPG-09 | MPG-10 | MPG-11 | MPG-05R | Tocopheryl succinate salt 1:1 |
|---|---|---|---|---|---|---|
| Internal water phase | | | | | | |
| GA, mg | 30.1 | 30.1 | 30.1 | 30.1 | 30.9 | 30.1 |
| GA dry base, mg | 25.0 | 25.0 | 25.0 | 25.0 | 25.6 | 25.0 |
| Water, μl | 150 | 200 | 200 | 200 | 200 | 200 |
| Polymer | | | | | | |
| PLGA RG 502H, mg | 165 | 165 | | | 165 | |
| PLGA RG-503, mg | | | 165 | 165 | | 0 |
| Oil phase | | | | | | |
| Tocopheryl succinate, mg | 20 | 50 | 20 | 50 | 0 | 10 |
| Methylene chloride | 2.7 g | 2.7 g | 2.7 g | 3.2 g | 3.7 g | 2 g |
| External water phase | | | | | | |
| Surfactant | 30 ml 0.5% PVA | 30 ml 0.5% PVA | 30 ml 0.2% Tw80 | 30 ml 0.5% PVA | 30 ml 0.5% PVA | 20 ml $H_2O$ |
| NaCl | 0.25 g | 0.25 g | 0.25 g | 0.25 g | 0.25 g | — |
| Preparation process description (processor, speed set, evaporation duration) | OMNI GLH #4 1 min, evap. 4 hr RT mag. stirrer | OMNI GLH #4 1 min, evap. 4 hr RT mag. stirrer | OMNI GLH #4 1 min, evap.4 hr RT mag. stirrer | OMNI GLH #4 1 min, evap.4 hr RT mag. stirrer | IKA VDI-12 #5 2 min, evap.4 hr RT mag. stirrer | 22 kHz Titanium indenter sonication 13 W 60 sec |

TABLE 4-continued

PLGA microparticles for sustained release of glatiramer acetate (GA) (formulations 05R, 08-011 and tocopheryl succinate salt of glatiramer)

| | MPG-08 | MPG-09 | MPG-10 | MPG-11 | MPG-05R | Tocopheryl succinate salt 1:1 |
|---|---|---|---|---|---|---|
| Microparticles description | Spherical MP 2-5 μm smooth | Spherical MP 1-3 μm smooth | Spherical MP 3-5&20 μm smooth | Spherical MP 2-4 μm smooth | Spherical MP 1-10 μm with inclusions | Spherical agglomerate 30-100 μm |
| Binding (association with MPs) | 82% | 87% | 46% | 85% | 93% | 89% |

Formulation of an equimolar complex (salt) of tocopheryl succinate (MW 530, one COOH eq. 265 Dalton) and glatiramer acetate (MW 4,700-11,000, one $NH_2$ eq. ~693 Dalton) was prepared by suspending an aqueous solution of glatiramer in methylene chloride with previously dissolved equimolar amount of tocopheryl succinate with the help of an ultrasonic indenter for 60 seconds (6×10 sec) with ice cooling. After evaporation of the organic solvent and water, the thus formed water insoluble product was collected, washed with purified water and with dry ethanol and used for further investigations without additional purification.

TABLE 5

PLGA microparticles for sustained release of glatiramer acetate (GA) (formulations MPG-12-15)

| | MPG-12 | MPG-13 | MPG-14 | MPG-15 |
|---|---|---|---|---|
| Internal water phase | | | | |
| GA, mg | 31.8 | 31.8 | 31.5 | 31.7 |
| GA dry base, mg | 26.4 | 26.4 | 26.1 | 26.3 |
| Water, μl | 200 | 200 | 200 | 200 |
| Polymer in the oil phase | | | | |
| PLGA RG 502H, mg | 200 | 250 | 300 | 165 |
| Oil phase | | | | |
| Tocopheryl succinate, mg | | | | 9 |
| Methylene chloride | 2.6 g | 2.7 g | 2.7 g | 2.6 g |
| External water phase | | | | |
| 0.5% PVA solution | 30 ml | 30 ml | 30 ml | 30 ml |
| NaCl | 0.25 g | 0.25 g | 0.25 g | 0.25 g |
| Preparation process description (processor, speed set, evaporation duration) | IKA VDI-12 #5 (1 min), evaporation 4 hr RT magnetic stirrer | IKA VDI-12 #5 (1 min), evaporation 4 hr RT magnetic stirrer | IKA VDI-12 #5 (1 min), evaporation 4 hr RT magnetic stirrer | IKA VDI-12 #6 20 sec, #5 40 sec, evaporation 4 hr RT magnetic stirrer |
| Microparticles description | spherical particles 10-15 μm with inclusions | spherical particles 10-18 μm with inclusions | spherical particles 10-15 μm with inclusions | spherical particles 6-10 μm with inclusions; aggregates |
| Binding (association with MPs) | 85.4% | 94.9% | 96.4% | 70.9% |
| Burst (release at 1 hour) | 18.9% | 8.5% | 9.5% | 13.6% |
| Amount of GA, released between day 4 and day 11 | 25.6% | 21.0% | 32.7% | 19.6% |

TABLE 5A

*Calculation Table for Formulations MPG-01 to MPG-15*
*These calculations show the weight ratio of glatiramer acetate ("GA") to poly (D,L-lactide-co-glycolide) ("PLGA") in Formulations MPG-01 to MPG-15 of Tables 2 to 5 based on the amounts of GA and PLGA present in those formulations. These calculations show that the weight ratio of GA:PLGA ranges from 1:5.2 to 1:15.9.*

| | Formulations of Table 2: | | | |
|---|---|---|---|---|
| | MPG-01 | MPG-02 | MPG-03 | MPG-04 |
| GA, mg | 17 | 60.25 | 30 | 18.7 |
| PLGA RG 502H, mg | 270 | — | — | 165 |
| PLGA RG 502, mg | — | 500 | 220 | — |
| Ratio of GA:PLGA | 1:15.9 | 1:8.3 | 1:7.3 | 1:8.8 |

| | Formulations of Table 3: | | |
|---|---|---|---|
| | MPG-05 | MPG-06 | MPG-07 |
| GA, mg | 30.8 | 20 | 20 |
| PLGA RG 502H, mg | 165 | — | — |
| PLGA RG 502, mg | — | 200 | 250 |
| Ratio of GA:PLGA | 1:5.4 | 1:10 | 1:12.5 |

| | Formulations of Table 4: | | | | |
|---|---|---|---|---|---|
| | MPG-08 | MPG-09 | MPG-10 | MPG-11 | MPG-05R |
| GA, mg | 30.1 | 30.1 | 30.1 | 30.1 | 30.9 |
| PLGA RG 502H, mg | 165 | 165 | — | — | 165 |
| PLGA RG-503, mg | — | — | 165 | 165 | — |
| Ratio of GA:PLGA | 1:5.5 | 1:5.5 | 1:5.5 | 1:5.5 | 1:5.3 |

| | Formulations of Table 5: | | | |
|---|---|---|---|---|
| | MPG-12 | MPG-13 | MPG-14 | MPG-15 |
| GA, mg | 31.8 | 31.8 | 31.5 | 31.7 |
| PLGA RG 502H, mg | 200 | 250 | 300 | 165 |
| PLGA RG-503, mg | — | — | — | — |
| Ratio of GA:PLGA | 1:6.3 | 1:7.9 | 1:9.5 | 1:5.2 |

Lyophilization

Microparticulate formulations after centrifugation and washing were lyophilized either "as is", following sediment re-suspension in purified water, or in some cases, with the addition of cryoprotectant (sediment was re-suspended in a 5% mannitol solution). Samples were frozen for 1 hour at −37-43° C. using the lyophilizer plate, and freeze-dried using lyophilizer "Alpha 2-4 LSC" (Christ, Germany) for 24-48 hours at pressure 0.050 mbar and −20° C., final drying at 0.025 mbar and +20° C. for 10-16 hours. In both re-suspension procedures the lyophilized product could be easily reconstituted. The use of mannitol lead to a readily reconstituted product as compared to formulations without the cryoprotectant, but such compositions contained significant amount of ballast material and required more complex calculations to determine the real concentration of the active material.

Example 4

In vitro Release of Glatiramer Acetate from PLGA Microparticles

Equipment
20 ml vials
multi-point magnetic stirrer
Incubator
Pipettors
UV-Vis spectrophotometer Shimadzu 1601
Reagents and plastic/glassware
Test-Articles Formulations MPG-02, 03, 04, 05, 05R, 06, 07, 12, 13, 14, and 15-50 mg of dry lyophilized microparticles.

Formulations MPG-08, 09, 10, and 11—amount corresponding to 50 mg of dry microparticles, lyophilized with 5% mannitol.

Control glatiramer acetate solution 20-50 μg/mL (as base) in PBS with 0.05% sodium azide)

Temperature: 37° C.

In order to evaluate the release of incorporated glatiramer acetate from biodegradable PLGA microparticles loaded with glatiramer acetate (various formulations), the following process had been employed.

Process description: 20 ml of PBS (0.01M phosphate, 0.05% $NaN_3$) pH 7.4 were added to each vial. The vials were placed at 37° C. and stirred with a small magnet. 600 μl samples were centrifugated at 10,000 g for 5 minutes. 500 μl of supernatant were transferred to a 1.5 ml microtube followed by the addition of 500 μl of 0.1M borate buffer (2-fold dilution) and 50 μl TNBS. The resulting composition was torturously mixed and was kept on the bench for 30 minutes. Analysis was performed using TNBS method.

The remaining precipitated particles, re-suspended with 500 μl of fresh PBS (with $NaN_3$), were returned to the vial. Correct calculation for released amount of glatiramer acetate was performed in further release process for 2.5% for each time-point.

The release of the incorporated glatiramer acetate was carried out in tightly closed 20 ml glass vials, using incubator at 37° C., equipped with a multi-point magnetic stirrer. Phosphate buffered saline (PBS) with pH 7.4 was used as a release media.

The release of the glatiramer acetate was tested over a period of 10-32 days.

The equation for the calibration curve in the range 1-200 μg/ml was calculated (Shimadzu UV-1601) as:

$$OD=0.035+0.0132*C(r^2=0.9985)$$

Where OD—optical density (difference at 420 and 700 nm)

C—concentration of glatiramer acetate base, μg/ml

Results of peptide release of formulations MPG01-MPG07 are shown in FIG. 1. The fastest release of the incorporated glatiramer acetate (40% for days 1-10) was obtained in formulation MPG-05, based on low molecular weight PLGA polymer with acidic end groups (Resomer RG 502H) and without hydrophobic counter-ion. Neutral polymer RG 502 with relatively small amount of tocopheryl succinate as a counter-ion (MPG-03) also demonstrated significant release (~30% for days 2-12), but with lower absolute release values. Formulations containing higher amounts of counter-ions showed suppression of the drug release. Without being bound by any theory or mechanism of action, this might be attributed to the high hydrophobicity of the formed complex. Additionally, the preparation of the microparticles with DCP or DMPG was associated with the formation of aggregates and a wide particle size distribution.

The use of a bigger and more powerful high shear mixer OMNI GLH (shaft diameter 20 mm, 5000-30000 rpm instead of VDI-12 (12 mm shaft) leads to a significant decrease in the size of microparticles (formulations 8-11) and increased surface smoothness. Increasing of amount of the organic solvent (MPG-02) caused decreased peptide incorporation into the microparticles. Without being bound by any theory or mechanism of action, this is possibly attributed to the increase of the intermediate o/w/o double emulsion droplet size. Similarly, the use of polysorbate as non-ionic surfactant also negatively affected the drug loading (MPG-10 with 0.2% Tween-80). The addition of hydrophobic counter-ions (tocopheryl succinate, dimyristoylphosphatidylglycerol DMPG, dicetylphosphate DCP) significantly retarded peptide release from the polymeric microparticles in comparison to formulations without counter-ion (MPG-05, MPG-05R). Without being bound by any theory or mechanism of action, the addition of the hydrophobic counter-ions may provide microparticles with compromised properties (MPG-06).

The chemical structure of the polymer used showed a greater impact on the release properties than the molecular weight of the PLGA. Resomers RG 502H and RG 502 (MW about 17,000 Dalton) had very similar diffusion coefficients, but the main factor determining the release of the included peptide form the polymeric matrix was a multi-point ionic interaction between positively charged Lys moieties of glatiramer acetate and carboxylic end groups in PLGA polymer. Neutral Resomer® RG 502 showed a low binding capacity even in the presence of a counter-ion (MPG-02, 03) while neutral Resomer® RG 503 with higher molecular weight demonstrated better binding but very slow release (MPG-10, 11).

Figure 2:
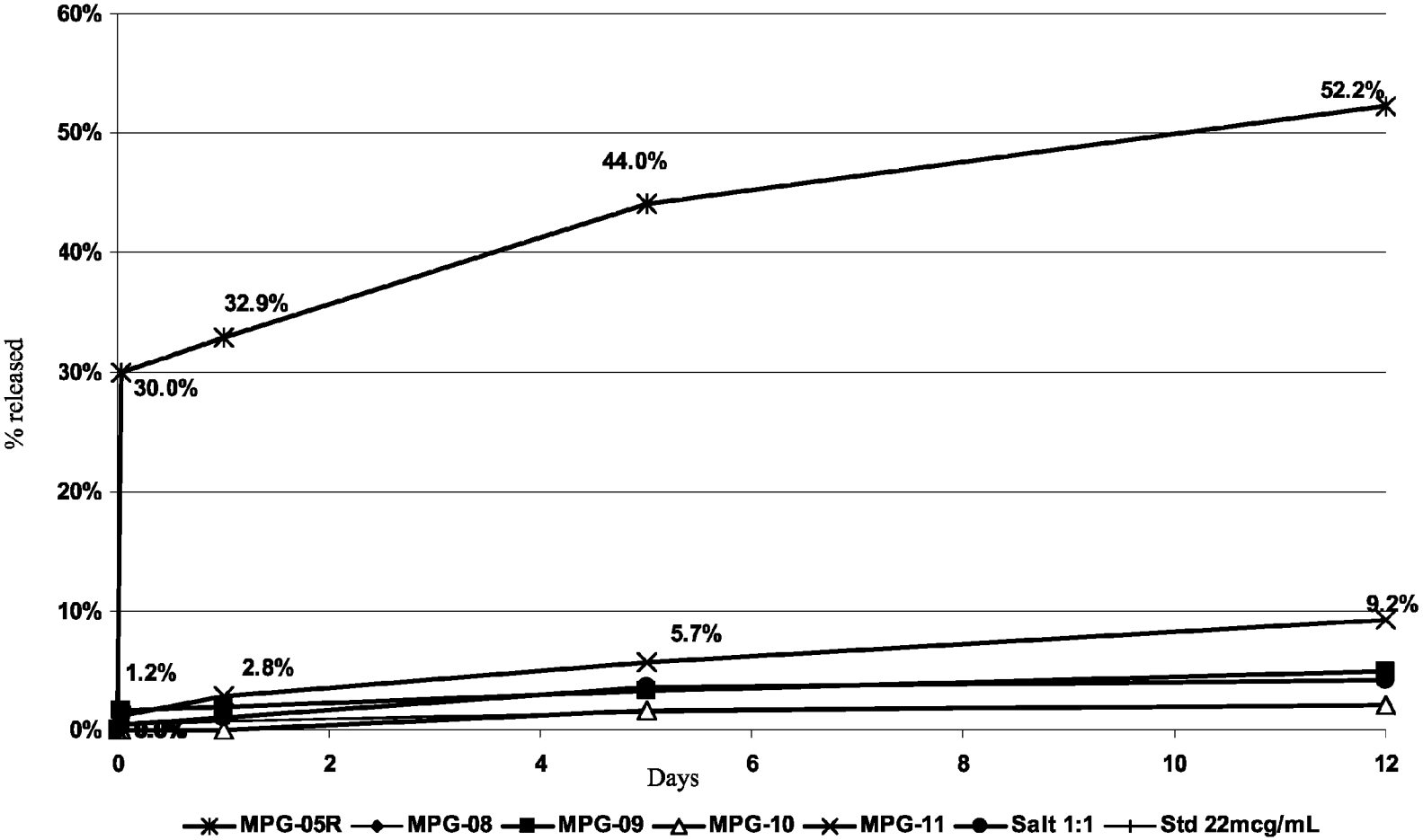
FIG. 2. Release of glatiramer acetate from PLGA microparticulate formulations MPG-05R, 08-11 and tocopheryl succinate salt of glatiramer (1:1) in PBS at 37° C. Data represented are normalized to standard peptide solution stored in same conditions.

Repeated release experiments from separately prepared identical formulations (MPG-05 and MPG-05R) showed reasonably similar behavior and a good reproducibility for such small-scale batches. Formulations of glatiramer acetate with Resomer® RG 502H demonstrated a similar burst effect (~30%), good initial peptide binding and fast drug release (FIG. 2).

Formulation of an equimolar complex (salt) of tocopheryl succinate had a high binding and extremely low water solubility (~5 μg/ml). Without being bound by any theory or mechanism of action, this may be caused by an ionic cross-linking of the diacid (tocopheryl succinate) and the polyamine molecule of the polymer. Release of the polymer from this salt in PBS was extremely slow. For polymeric microparticles, when tocopheryl succinate incorporated into the PLGA matrix, only part of this diacid can interact with the polymer, and for complete release suppression higher amount of tocopheryl succinate is required. So release rate may be regulated by the ratio between the glatiramer and PLGA. The amount of organic solvent used may also be of importance but to a lower extent.

Figure 3:
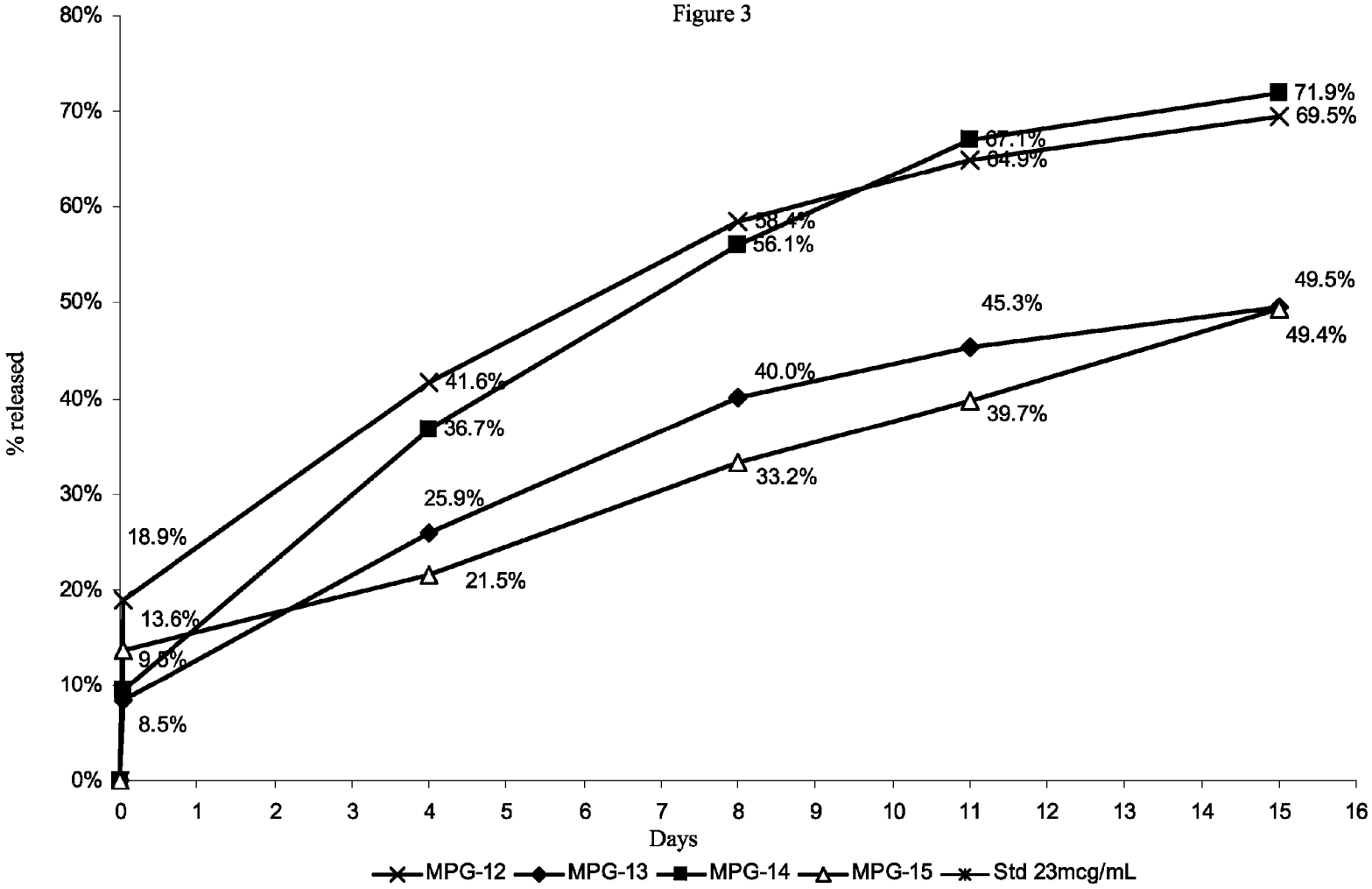
FIG. 3. Release of glatiramer acetate from PLGA microparticulate formulations MPG-12-15 in PBS at 37° C. The data presented are normalized to standard peptide solution stored in same conditions.

Formulations 12-15, based on Resomer® RG 502H with different ratios between the drug and the polymer, showed that the ratio plays an important role in controlling the initial burst effect, the binding level and the release rate. The adjustment of the amount of the PLGA and the peptide as well as the addition of a hydrophobic counter-ion, such as tocopheryl succinate, allows the preparation of microparticulate formulations (MPG-12-15) with high binding, low initial burst and reasonable release rates (FIG. 3).

Example 5

Up Scaling

Lyophilized Samples of Glatiramer Acetate Microparticulate Formulations

MPG-14 SU-1—formulation of MPG-014, was produced using a bigger reaction vessel and a bigger homogenizer (OMNI GLH) at low speed.

Total—13 vials; each vial contained approximately 235 mg of lyophilized formulation with total content of glatiramer acetate of ~18.2 mg per vial, equal to ~75 μg/mg of the lyophilized formulation.

MPG-15 SU-1—formulation of MPG-015, was produced using a bigger reaction vessel and a bigger homogenizer (OMNI GLH) at low speed.

Total—10 vials; each vial contained approximately 145 mg of lyophilized formulation with total content of glatiramer acetate of ~14.9 mg per vial, equal to ~100 μg/mg of the lyophilized formulation.

MPG-14 SU-2—formulation of MPG-014, was produced using the same reaction vessel, the same homogenizer (VDI 12) and the same parameters, process repeated several times. Composition was washed thoroughly to decrease initial burst.

Total—12 vials; each vial contained approximately 88 mg of lyophilized formulation with total content of glatiramer acetate of ~6.3 mg per vial, equal to ~72 μg/mg of the lyophilized formulation.

MPG-15 SU-2—formulation of MPG-015, was produced using the same reaction vessel, the same homogenizer (VDI 12) and the same parameters, process repeated several times. Composition was washed thoroughly to decrease initial burst.

Total—12 vials; each vial contained approximately 55 mg of lyophilized formulation with total content glatiramer acetate of ~5.6 mg per vial, equal to ~100 μg/mg of the lyophilized formulation.

All lyophilized samples were stored in a refrigerator at +4° C. and were reconstituted before use.

Figure 4:
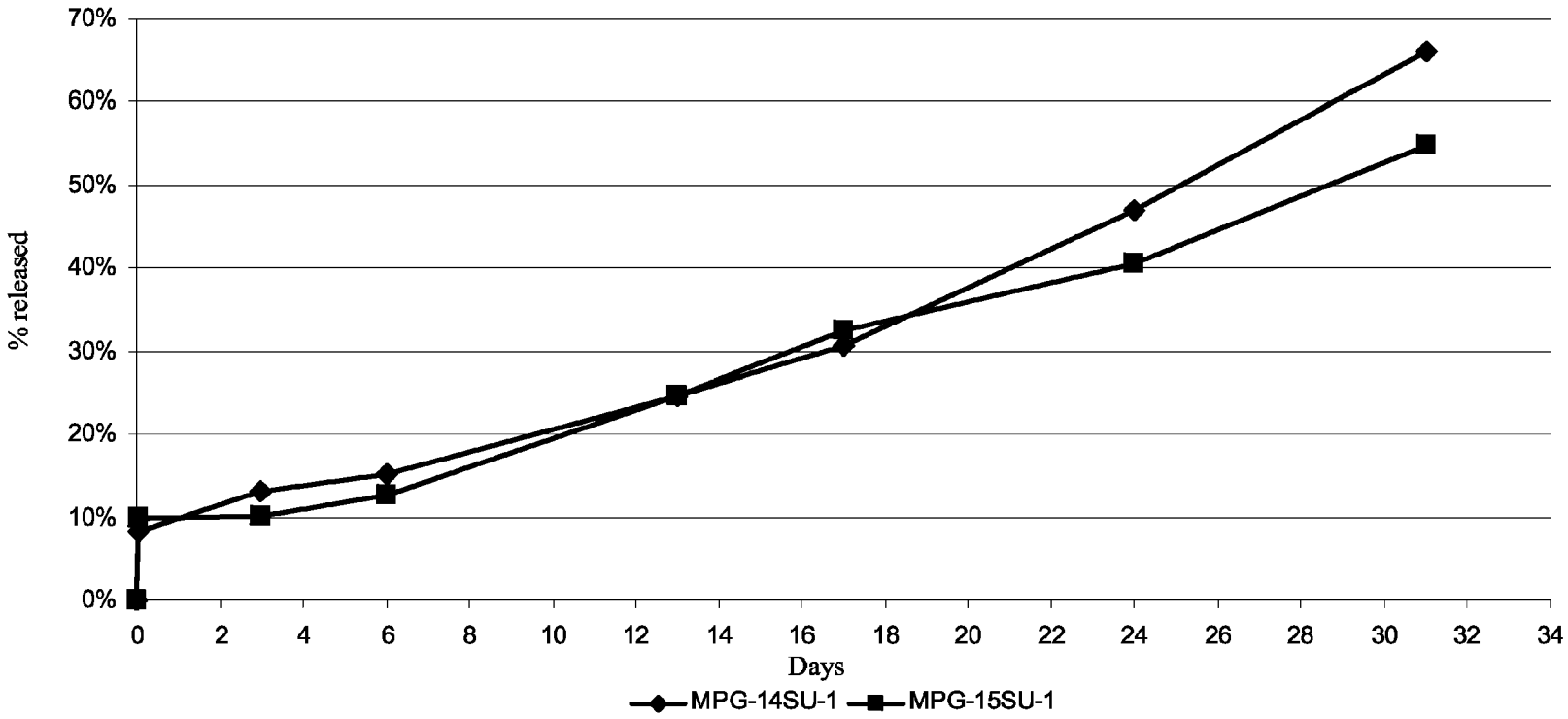
FIG. 4. Release of glatiramer acetate from PLGA microparticulate formulations MPG-14SU-1 and MPG-15SU-1 in vitro in PBS at 37° C., pH 7.4.
Figure 5:
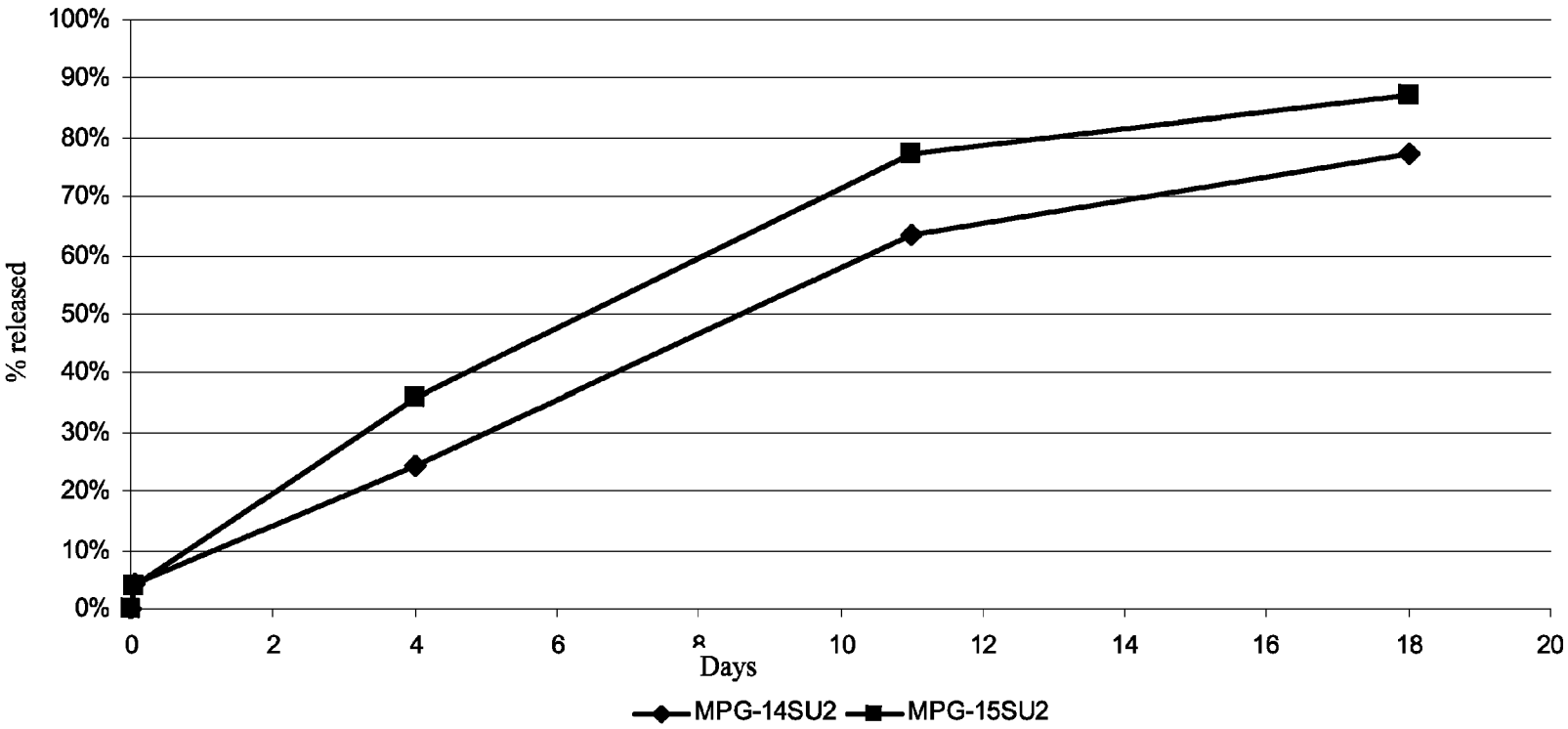
FIG. 5. Release of glatiramer acetate from PLGA microparticulate formulations MPG-14SU-2 and MPG-15SU-2 in vitro in PBS at 37° C., pH 7.4.

The ratio between the formulation and the diluent (glucose solution) was at least 1:5, preferably 1:10 and higher. Vigorous shaking was performed prior to the administration of the reconstituted sample. Release profiles of these formulations are shown in FIGS. 4 and 5.

Thus, the incorporation of the highly water soluble peptide of glatiramer acetate into a biodegradable polymeric microparticles was demonstrated. The microparticles showed good binding of the polymer, reasonable drug loading and reduced initial release burst which can be regulated by employing different compositions and processes of preparation. PLGA microparticles, made of Resomer® 502H and loaded with glatiramer acetate, provide in vitro release of the incorporated peptide with release rate of 3-5% per day for 10-15 days in a stirred aqueous media (phosphate buffered saline, pH 7.4) at 37° C.

Example 6

Experimental Autoimmune Encephalomyelitis (EAE) Model

Experimental autoimmune encephalomyelitis (EAE) is an inflammatory autoimmune demyelinating disease which can be induced in laboratory animals. Such disease has become the standard laboratory model for studying clinical and experimental autoimmune diseases. In fact, numerous articles (e.g., Abramsky et. al., J Neuroimmunol (1982) 2 1 and Bolton et al., J Neurol Sci. (1982) 56 147) note that the similarities of chronic relapsing EAE in animals to multiple sclerosis in humans especially implicates the value of EAE for the study of autoimmune demyelinating diseases such as multiple sclerosis. As such, the EAE test model was employed to establish the activity of the formulations of the present invention against multiple sclerosis.

In the following example, the glatiramer acetate microparticulate formulation designated above as MPG-14 was used and compared to a conventional glatiramer acetate injectable formulation. The conventional formulation is designated herein as "GA", and the microparticulate depot formulation of the invention is designated as "GA-depot". The effect of the two formulations on MOG (myelin-oligodendrocyte-glycoprotein)-induced chronic EAE in C57BL/6 mice was examined according to the procedure described below.

Forty (40) female C57BL/6 mice had been randomly grouped into three (3) groups by body weight in this study; each group consisted of ten (10) mice. The different groups and the dosing regimens are detailed in Table 6. EAE had been induced by injection of emulsion of MOG subcutaneously on the shaved back of the mouse at three sites, followed by an intraperitoneal injection of Bordetella pertussis toxin in PBS on Day 0 and 48 hours post MOG immunization. EAE had been assessed by clinical scoring of the mice once daily from Day 0 to Day 14 post immunization. The disease incidence and group mean score had been determined and all treatment groups had been compared to non-treatment control. On Day 14, mice had been terminated.

Test Article Preparation:

GA was dissolved in water-for-injection (WFI). GA depot was suspended in WFI, vortexed and if necessary sonicated for up to 10 minutes without heating, until a homogenous white suspension was obtained, capable to be withdrawn and injected via an adequate needle.

Vehicle Information:

Vehicle 1: saline, 0.9% NaCl in sterile water

Vehicle 2: water for injection (WFI)

Reagents:

MOG 35-55: (GL BiochemCo. Ltd; Shanghai, P.R. China). MOG 35-55 had been dissolved in saline to a concentration of 2 mg/mL.

Complete Freund's adjuvant (CFA) (Cat: F5881; Sigma-Aldrich; St. Louis, Mo., USA). Heat-killed Mycobacterium tuberculosis strain H37RA (Cat: 231141; Difco; Detroit, Mich., USA) were added to complete Freund's adjuvant to a final concentration of 4 mg/mL.

Bordetella pertussis toxin (PTX): (Cat: P7208; Sigma-Aldrich; St. Louis, Mo., USA)

Using a high-speed homogenizer, the above MOG solution had been emulsified with equal volume of the modified CFA on ice for 30,000 rpm for 1.5 hour.

Animals:

C57BL/6 mice, female, 7-9 weeks, 17-20 g Adaptation: not less than 7 days.

Room: Specific Pathogen Free (SPF) room

Room temperature: 20-26° C.

Room relative humidity: 40-70%

Light cycle: fluorescent light for 12-hour light (08:00-20:00) and 12-hour dark.

Animal hosting: 3-4 mice/cage by treatment group

Food: free access to food (irradiated, Shanghai SLAC Laboratory Animal Co. Ltd., China).

Water: free access to water (municipal tap water filtered by Mol Ultrapure Water System).

Allocation to Treatment Groups:

Animals had been assigned to treatment groups by randomization in Biobook software to achieve similar group mean weight, which provides for control of bias.

TABLE 6

| Group and dosing regimen | | | | | | | | |
|---|---|---|---|---|---|---|---|---|
| | | | | | Dosage | | | |
| Group | Test article | N | Route | Conc. mg/ml | mL/mice/day | mg/mice/day | Regimen | Dose on |
| 1 | vehicle[a] | 10 | s.c | N/A | 0.2 | N/A | q.d. | day 0-day 9 |
| 2 | GA-depot[b] | 10 | i.m | 335* | 0.2 | 67* | q.d. | day 0, day 1 |
| 3 | GA[b] | 10 | i.m | 25 | 0.2 | 5 | q.d. | day 0, day 1 |

[a]Vehicle is saline

[b]Vehicle is WFI

*GA content is 75 mg/g of "GA-depot" formulated product, i.e. 5 mg/mice/day of GA After anesthetization by isoflurane (2-3%, inhalation), EAE had been induced by injecting 100 μL emulsion subcutaneously into the shaved backs of the mice. Bordetella pertussis toxin (200 ng in 200 μL of PBS) had been administered i.p. on the day of immunization (Day 0) and 48 hours thereafter.

Test article or vehicle had been administrated to each group according to the treatment regimes and dosing described in Table 6. Mice in group 1 had been administered subcutaneously, once-daily, for 10 consecutive days. Group 2—a total dose of 10 mg active per mice had been divided into 2 doses, each of 5 mg active ingredient (67 mg formulated product), administered intramuscularly on day 0 and day 1. Group 3—a total dose of 10 mg active ingredient per mice had been divided into 2 doses, each of 5 mg active, administered intramuscularly on day 0 and day 1.

Body weight of all mice had been recorded daily starting from Day 0 to Day 14. EAE development had been assessed by clinically scoring of the mice once daily from Day 0 to Day 14 post immunization according to a scale of 0-5 (0=normal mouse; 1=limp tail or hind limb weakness; 2=limp tail and hind limb weakness; 3=partial hind limb paralysis; 4=complete hind limb paralysis; and 5=moribund state). The incidence, mortality and group mean score had been determined and the treatment groups had been compared to non-treatment control. On Day 14, mice had been terminated.

Mean body weight among the groups had been compared by ANOVA followed by Dunnett's post-Hoc test. Comparisons of the mean clinical score between two groups had been made by Friedman test followed by Dunn's Multiple Comparison Test. Incidence of disease between two groups had been compared among the groups by Peason Chi-squwere test. $p<0.05$ had been considered significant.

Results:

Emulsified MOG induced an inflammatory response as evidenced by clinical manifestations in line with previous data.

Figure 6:
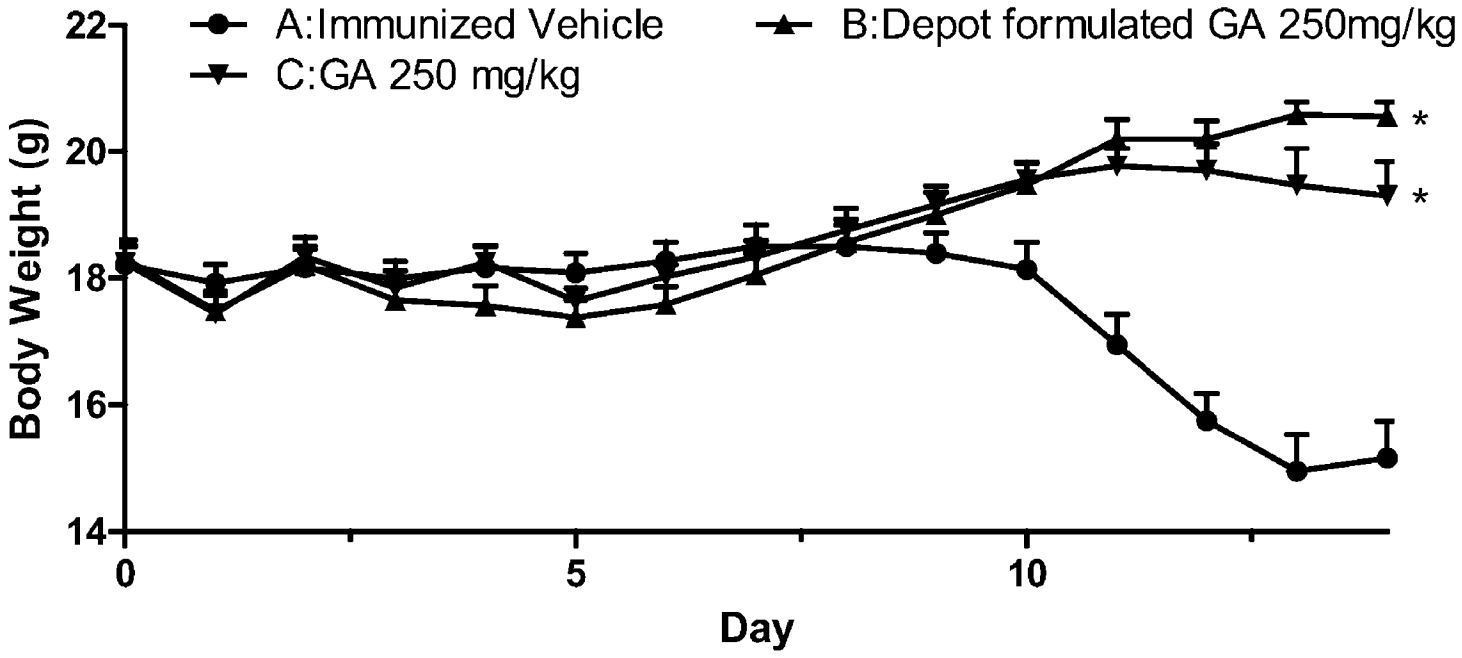
FIG. 6. Effect of glatiramer acetate (GA) depot formulation (B: depot formulated GA 250 mg/kg) versus conventional GA formulation (C: GA 250 mg/kg) and vehicle (A) on body weight in a mouse experimental autoimmune encephalomyelitis (EAE) model. ** $p<0.05$ compared with Immunized-Vehicle by Repeated Measures ANOVA.
Figure 7A:
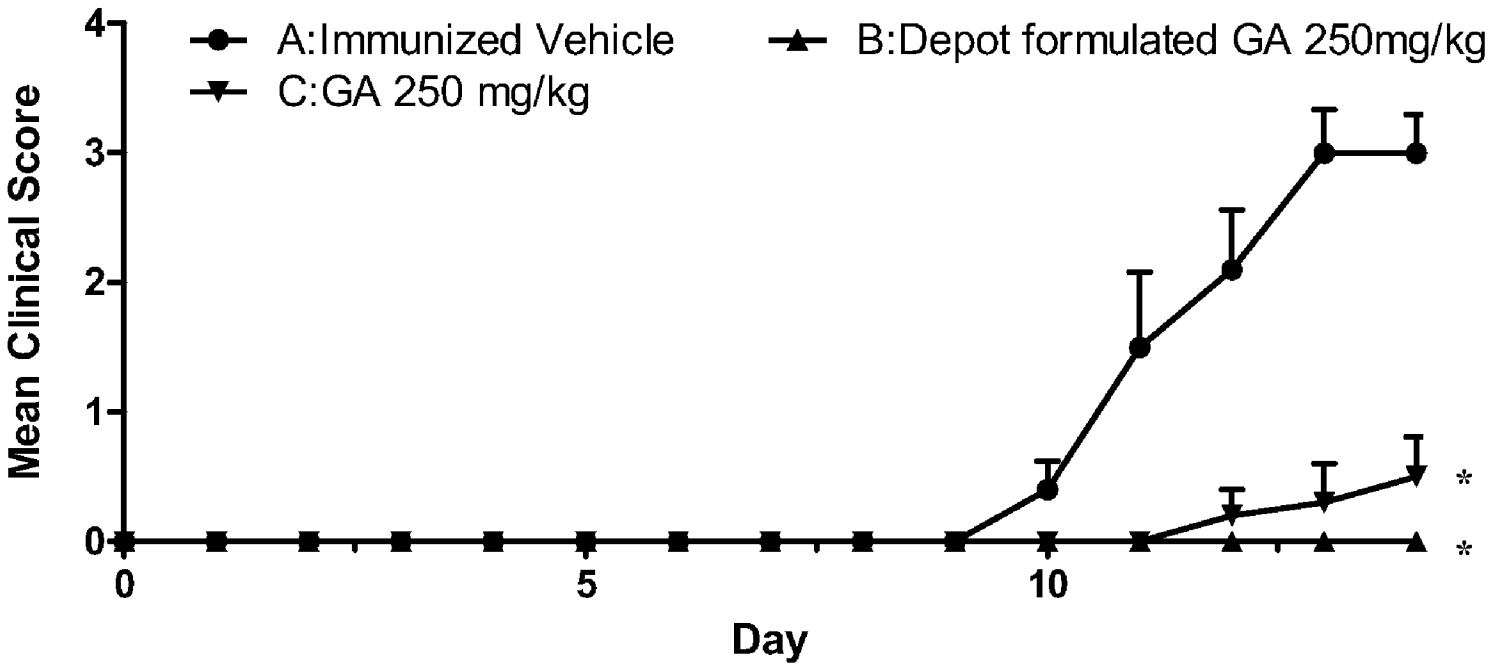
FIG. 7. Effect of glatiramer acetate (GA) depot formulation (B: depot formulated GA 250 mg/kg) versus conventional GA formulation (C: GA 250 mg/kg) and vehicle (A) on clinical score in a mouse EAE model. A) mean clinical score. * $p<0.05$ compared with Immunized Vehicle by Friedman test; B) AUC of clinical score.
Figure 7B:
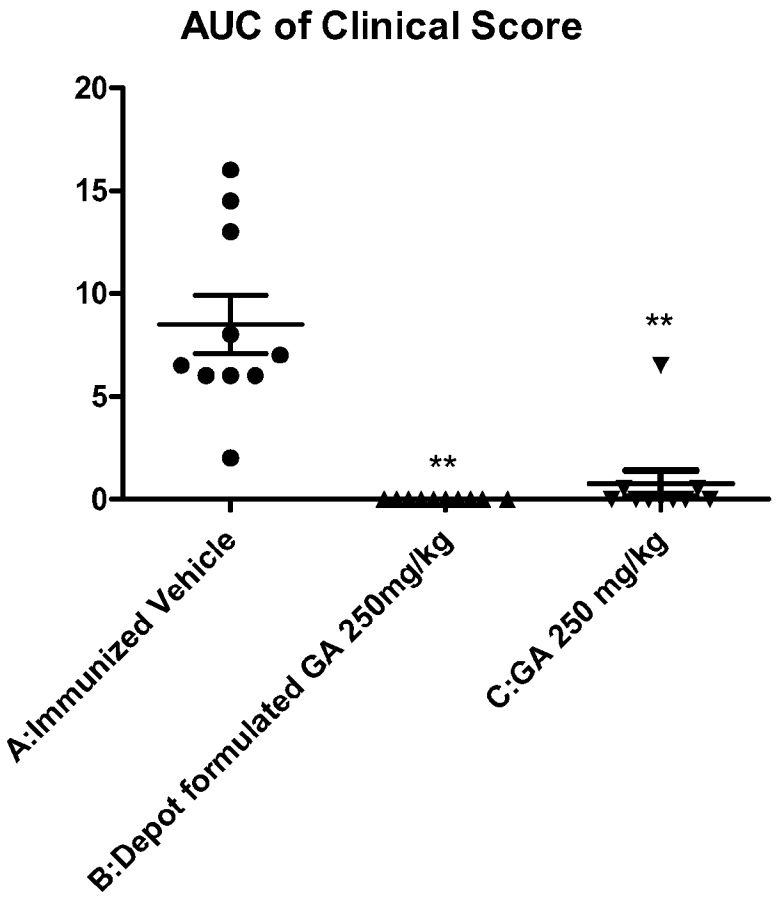
Figure 8:
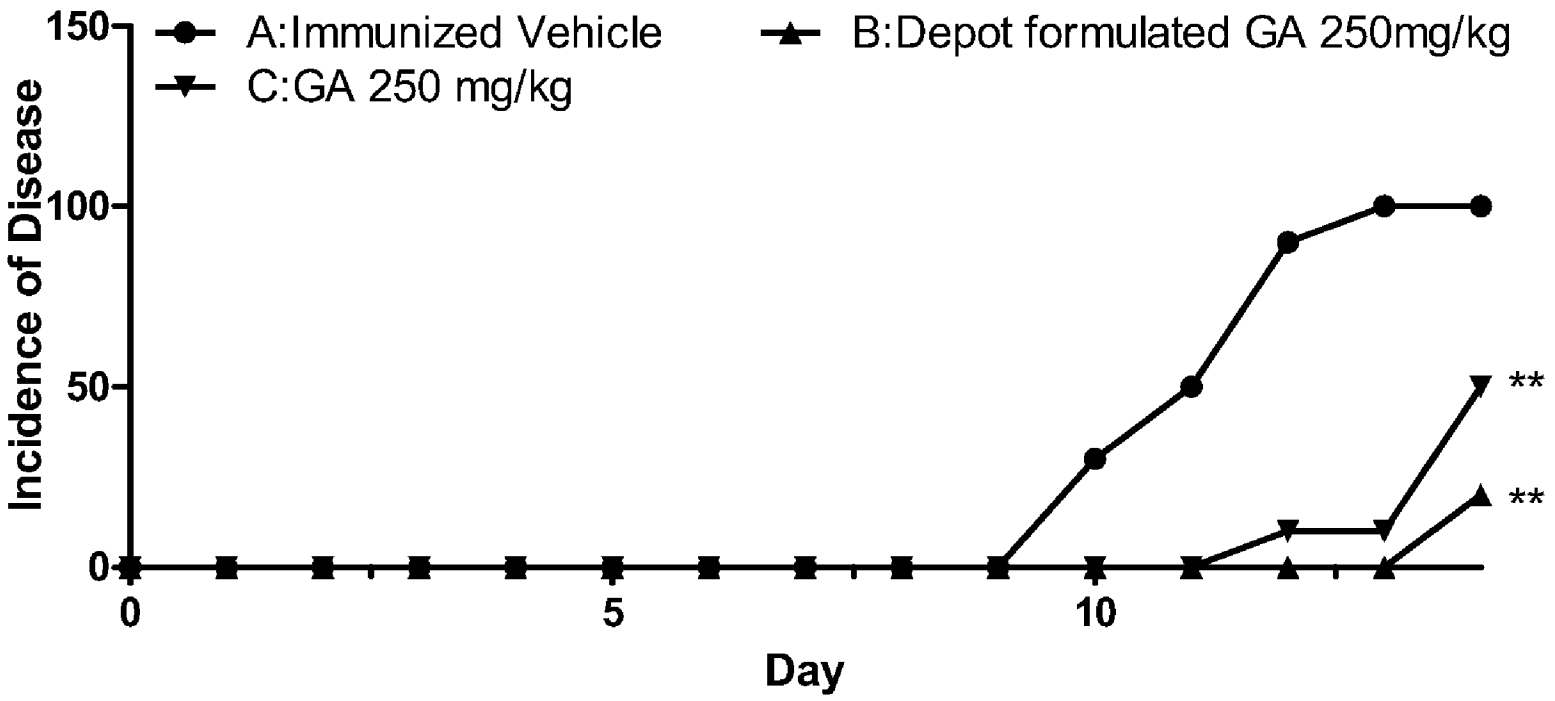
FIG. 8. Effect of glatiramer acetate (GA) depot formulation (B: depot formulated GA 250 mg/kg) versus conventional GA formulation (C: GA 250 mg/kg) and vehicle (A) on incidence of disease in a mouse EAE model. ** $p<0.01$ compared with Immunized Vehicle by Survival Analysis.

As can be seen in FIGS. 6, 7A+B, 8 and in Table 7, throughout the 14 days of the study GA depot completely prevented EAE development—it showed 100% inhibition rate, compared to about 91% inhibition by the conventional formulated GA. GA depot significantly prevented body weight loss and ameliorated clinical symptoms compared to vehicle control, and was more effective compared to GA.

Parameters including maximum score, disease duration and mean day of onset also indicated that GA depot significantly suppressed EAE development, similar to GA, as compared to vehicle.

Thus, GA formulated according to embodiments of the present invention is comparable or better than the conventional formulation when given at the same dosage level.

TABLE 7

| disease status summary (0-14 days) | | | | | | |
|---|---|---|---|---|---|---|
| Group | Maximum score | Disease duration | Mean day of onset | AUC 0-14 day clinical score | Inhibition rate | Mortality |
| 1 (vehicle) | 3.4 ± 0.31 | 3.70 ± 0.33 | 11.3 ± 0.33 | 8.50 ± 1.41 | N/A | 0% |
| 2 (GA-depot) | 0.0 ± 0.00** | 0.0 ± 0.00** | N/A** | 0.0 ± 0.00** | 100% | 0% |
| 3 (GA) | 0.5 ± 0.31** | 0.5 ± 0.31** | N/A** | 0.75 ± 0.64** | 91.18% | 0% |

**p < 0.01 statistically significant difference compared with Immunized Vehicle 1 (by Kruskal-Wallis test (for Maximun Score)/One-way ANOVA (for other parameters) followed by Dunn's/Dunnett's Multiple Comparison Test).

Example 7

In Vivo Studies Using the EAE Model

To determine the effect of the formulations of the present invention on the murine model of MS, experimental autoimmune encephalomyelitis (EAE) is performed. 25-hydroxyvitamin $D_3$-1α-hydroxylase knockout mice (1α-OH KO) are maintained on a purified diet containing 0.87% calcium and 1 ng $1,25\text{-}(OH)_2D_3$ (Vit D) for two to three weeks prior to EAE immunization. EAE is induced to mice at six to ten weeks of age, by subcutaneous immunization of 200 μg of the immunodominant peptide to myelin oligodendrocyte glycoproprotein ($MOG_{35-55}$).

The peptide is synthesized using standard 9-fluorenylmethoxy-carbonyl chemistry. The peptide is dissolved in Freund's complete adjuvant (CFA; Sigma) containing 4 mg/ml of heat-inactivated Mycobacterium tuberculosis H837a.

The mice are examined daily for clinical signs of EAE utilizing the following scoring system: 0, no sign; 1, limp tail; 2, hindlimb weakness; 3, hindlimb paralysis; 4, forelimb paralysis; 5, moribund or death.

Mice that develop clinical signs of EAE with scores ≥2 are treated with the formulation of the present invention which is administered by injection every week/two weeks/once a month at various dosages. Control groups are treated either with placebo or with Gold standard regimen of glatiramer acetate [e.g. PNAS, 2005, vol. 102, no. 52, 19045-19050]. Mice are then weighed and scored daily for symptoms of EAE. Statistical analysis is performed using the two-tailed Fisher exact probability test on incidence rates and the unpaired Student's t-test on all other measurements. Values of $P<0.05$ are considered statistically significant.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A long acting parenteral pharmaceutical composition comprising a therapeutically effective amount of a pharmaceutically acceptable salt of glatiramer, the composition being in a sustained release depot form which releases a therapeutically effective amount of the pharmaceutically acceptable salt of glatiramer over a period of about one week to about 6 months.

[2. The pharmaceutical composition according to claim 1, comprising a therapeutically effective amount of a pharmaceutically acceptable salt of glatiramer in depot form suitable for implantation at a medically acceptable location in a subject in need thereof.]

3. The pharmaceutical composition according to claim 1, wherein the pharmaceutically acceptable salt of glatiramer is glatiramer acetate.

[4. The pharmaceutical composition according to claim 1, in depot form suitable for subcutaneous or intramuscular implantation.]

5. The pharmaceutical composition according to claim 1, wherein the glatiramer comprises L-alanine, L-glutamic acid, L-lysine, and L-tyrosine in molar ratios of about 0.14 glutamic acid, about 0.43 alanine, about 0.10 tyrosine and about 0.33 lysine.

6. The pharmaceutical composition according to claim 1, wherein the glatiramer comprises about 15 to about 100 amino acids.

7. The pharmaceutical composition according to claim 1, further comprising a pharmaceutically acceptable biodegradable or non-biodegradable carrier.

8. The pharmaceutical composition according to claim 7, wherein the carrier is selected from poly (D,L-lactide-co-glycolide) (PLGA), poly (D,L-lactide) (PLA), polyglycolides (PGA), polycaprolactone, polyhydroxybutyrate, polyorthoesters, polyalkaneanhydrides, gelatin, collagen, oxidized cellulose, and polyphosphazene.

[9. The pharmaceutical composition according to claim 1 in the form of microparticles prepared by a water-in oil-in water double emulsification process.]

[10. The pharmaceutical composition according to claim 1 comprising an internal aqueous phase comprising a therapeutically effective amount of a pharmaceutically acceptable salt of glatiramer, a water immiscible polymeric phase comprising a biodegradable or non-biodegradable polymer and an external aqueous phase.]

[11. The pharmaceutical composition according to claim 10, wherein the water immiscible polymeric phase comprises a biodegradable polymer selected from poly (D,L-lactide) (PLA) and poly (D,L-lactide-co-glycolide) (PLGA) .]

[12. The pharmaceutical composition according to claim 10, wherein the external water phase comprises a surfactant selected form polyvinyl alcohol (PVA), polysorbate, polyethylene oxide-polypropylene oxide block copolymers and cellulose esters.]

[13. The pharmaceutical composition according to claim 1 in the form of biodegradable microspheres, non-biodegradable microspheres, implants of any suitable geometric shape, implantable rods, implantable capsules, implantable rings, or prolonged release gels or erodible matrices.]

[14. The pharmaceutical composition according to claim 1, wherein the composition provides equal or superior therapeutic efficacy to the commercially available daily injectable dosage forms of glatiramer acetate, with reduced incidence of side effects and/or with reduced severity of side effects at the local and/or systemic level.]

[15. The pharmaceutical composition according to claim 14, wherein the composition provides prolonged release or prolonged action of glatiramer in a subject as compared to a substantially similar dose of an immediate release formulation of glatiramer acetate.]

16. A method of treating multiple sclerosis comprising the step of parenterally administering to a subject in need thereof a long acting pharmaceutical composition comprising a therapeutically effective amount of a pharmaceutically acceptable salt of glatiramer, the composition being in a sustained release depot form which releases a therapeutically effective amount of the pharmaceutically acceptable salt of glatiramer over a period of about one week to about 6 months.

17. The method according to claim 16, wherein the long acting pharmaceutical composition comprises a therapeutically effective amount of a pharmaceutically acceptable salt of glatiramer in depot form suitable for implantation at a medically acceptable location in a subject in need thereof.

18. The method according to claim 17, comprising the step of implanting into a subject in need thereof the long acting pharmaceutical composition.

19. The method according to claim 16, comprising the step of subcutaneously or intramuscularly administering the pharmaceutical composition.

20. The method according to claim 16, wherein the pharmaceutical composition comprises glatiramer acetate.

21. The method according to claim 20, wherein the glatiramer acetate comprises L-alanine, L-glutamic acid, L-lysine, and L-tyrosine in the molar ratios of about 0.14 glutamic acid, about 0.43 alanine, about 0.10 tyrosine and about 0.33 lysine.

22. The method according to claim 21, wherein the glatiramer comprises about 15 to about 100 amino acids.

23. The method according to claim 16, wherein the pharmaceutical composition further comprises a pharmaceutically acceptable biodegradable or non-biodegradable carrier.

[24. The method according to claim 16, wherein the pharmaceutical composition is in the form of microparticles prepared by a water-in oil-in water double emulsification process.]

[25. The method according to claim 16, wherein the pharmaceutical composition comprises an internal aqueous phase comprising a therapeutically effective amount of a pharmaceutically acceptable salt of glatiramer, a water immiscible polymeric phase comprising a biodegradable or non-biodegradable polymer and an external aqueous phase.]

[26. The method according to claim 16, wherein the pharmaceutical composition is in the form of biodegradable microspheres, non-biodegradable microspheres, implants of any suitable geometric shape, implantable rods, implantable capsules, or implantable rings, prolonged release gels or erodible matrices.]

*27. The method according to claim 16, wherein the pharmaceutically acceptable salt of glatiramer is glatiramer acetate and the depot form contains between 20 mg and 750 mg of glatiramer acetate.*

*28. The method according to claim 27, comprising administering the depot form at a dosing regimen ranging from once every 2 weeks to once monthly.*

*29. The method according to claim 23, wherein the carrier is selected from poly (D,L-lactide-co-glycolide) (PLGA), poly (D,L-lactide) (PLA), polyglycolides (PGA), polycaprolactone, polyhydroxybutyrate, polyorthoesters, polyalkaneanhydrides, gelatin, collagen, oxidized cellulose, and polyphosphazene.*

*30. A method of treating multiple sclerosis comprising the step of parenterally administering to a subject in need thereof a long acting pharmaceutical composition comprising a therapeutically effective amount of a pharmaceutically acceptable salt of glatiramer, and a pharmaceutically acceptable biodegradable or non-biodegradable carrier which provides the composition in a sustained release depot form which releases a therapeutically effective amount of the pharmaceutically acceptable salt of glatiramer over a period of one week to 6 months, wherein the pharmaceutically acceptable salt of glatiramer is glatiramer acetate, the*

*depot form contains between 20 mg and 750 mg of glatiramer acetate and the carrier comprises a poly (D,L-lactide-co-glycolide) (PLGA).*

*31. A long acting parenteral pharmaceutical composition comprising a therapeutically effective amount of a pharmaceutically acceptable salt of glatiramer, and a pharmaceutically acceptable biodegradable or non-biodegradable carrier which provides the composition in a sustained release depot form which releases a therapeutically effective amount of the pharmaceutically acceptable salt of glatiramer over a period of about one week to about 6 months, wherein the pharmaceutically acceptable salt of glatiramer is glatiramer acetate, the depot form contains between 20 mg and 750 mg of glatiramer acetate, and the carrier comprises a poly (D,L-lactide-co-glycolide) (PLGA), wherein the depot form is prepared as a suspension for injection, and the suspension comprises microparticles.*

*32. The pharmaceutical composition according to claim 31, wherein the microparticles comprise double emulsion droplets comprising an internal aqueous phase comprising a therapeutically effective amount of a pharmaceutically acceptable salt of glatiramer, a water immiscible polymeric phase comprising a biodegradable or non-biodegradable polymer and an external aqueous phase.*

*33. The pharmaceutical composition according to claim 31, wherein preparation of the suspension for injection comprises, preparing microparticles comprising glatiramer acetate and PLGA by a water-in-oil-in-water double emulsification, drying the microparticles to form dried microparticles, and reconstituting the dried microparticles to form the suspension of the sustained release depot form for administration by injection.*

*34. A method for treating multiple sclerosis, comprising the step of injecting into a subject in need thereof the pharmaceutical composition according to claim 1.*

*35. A method for treating multiple sclerosis, comprising the step of injecting into a subject in need thereof the pharmaceutical composition according to claim 31.*

* * * * *